(12) United States Patent
Garidel et al.

(10) Patent No.: US 10,513,555 B2
(45) Date of Patent: Dec. 24, 2019

(54) ANTIBODY FORMULATIONS AND METHODS

(71) Applicant: Prothena Biosciences Limited, Dublin (IE)

(72) Inventors: Patrick Garidel, Norderstedt (DE); Andreas Langer, Maselheim (DE); Michael Grundman, San Diego, CA (US)

(73) Assignee: Prothena Biosciences Limited, Dublin (IE)

( * ) Notice: Subject to any disclaimer, the term of this patent is extended or adjusted under 35 U.S.C. 154(b) by 526 days.

(21) Appl. No.: 14/322,797

(22) Filed: Jul. 2, 2014

(65) Prior Publication Data

US 2015/0079074 A1    Mar. 19, 2015

Related U.S. Application Data

(60) Provisional application No. 61/843,011, filed on Jul. 4, 2013, provisional application No. 61/979,886, filed on Apr. 15, 2014.

(51) Int. Cl.
| | | |
|---|---|---|
| *A61K 39/395* | (2006.01) | |
| *C07K 16/18* | (2006.01) | |
| *A61K 47/26* | (2006.01) | |
| *A61K 9/19* | (2006.01) | |

(52) U.S. Cl.
CPC ........ *C07K 16/18* (2013.01); *A61K 39/39591* (2013.01); *A61K 9/19* (2013.01); *A61K 47/26* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 6,719,971 | B1 | 4/2004 | Carter et al. |
| 6,881,557 | B2 | 4/2005 | Foote et al. |
| 7,022,500 | B1 | 4/2006 | Queen et al. |
| 7,358,331 | B2 | 4/2008 | Chilcote et al. |
| 7,566,771 | B1 | 7/2009 | Adair et al. |
| 7,657,380 | B2 | 2/2010 | Lazar et al. |
| 7,674,599 | B2 | 3/2010 | Chilcote et al. |
| 7,910,133 | B2 | 3/2011 | Chilcote et al. |
| 7,919,088 | B2 | 4/2011 | Schenk et al. |
| 8,092,801 | B2 | 1/2012 | Schenk et al. |
| 8,609,820 | B2 | 12/2013 | Saldanha et al. |
| 8,790,644 | B2 | 7/2014 | Saldanha et al. |
| 9,217,030 | B2 | 12/2015 | Saldanha et al. |
| 9,234,031 | B2 | 1/2016 | Saldanha et al. |
| 9,556,259 | B2 | 1/2017 | Saldanha et al. |
| 9,605,056 | B2 | 3/2017 | Barbour et al. |
| 9,670,273 | B2 | 6/2017 | Saldanha et al. |
| 9,884,906 | B2 | 2/2018 | Saldanha et al. |
| 10,081,674 | B2 | 9/2018 | Barbour et al. |
| 10,084,674 | B2 | 9/2018 | Barbour et al. |
| 10,118,960 | B2 | 11/2018 | Saldanha et al. |
| 10,301,382 | B2 | 5/2019 | Barbour et al. |
| 2006/0008883 | A1 | 1/2006 | Lazar et al. |
| 2008/0014194 | A1 | 1/2008 | Schenk et al. |
| 2009/0010924 | A1 | 1/2009 | Wu et al. |
| 2009/0202432 | A1 | 8/2009 | Schenk et al. |
| 2009/0208487 | A1 | 8/2009 | Schenk et al. |
| 2010/0031377 | A1 | 2/2010 | Schenk et al. |
| 2010/0086545 | A1* | 4/2010 | Schenk ............. A61K 39/0007 424/133.1 |
| 2010/0098712 | A1* | 4/2010 | Adler .................. A61K 9/0019 424/172.1 |
| 2010/0203631 | A1 | 8/2010 | Chilcote et al. |
| 2010/0303827 | A1* | 12/2010 | Sharma, Sr. ...... A61K 39/39591 424/158.1 |
| 2011/0052498 | A1 | 3/2011 | Lannfelt et al. |
| 2012/0204275 | A1 | 8/2012 | Schenk |
| 2012/0276019 | A1 | 11/2012 | Charles et al. |
| 2013/0344088 | A1* | 12/2013 | Cosenza .......... A61K 39/39591 424/172.1 |
| 2014/0127131 | A1 | 5/2014 | Barbour et al. |
| 2014/0275495 | A1 | 9/2014 | Saldanha et al. |
| 2015/0024433 | A1 | 1/2015 | Saldanha et al. |
| 2015/0056187 | A1 | 2/2015 | Saldanha et al. |
| 2015/0079074 | A1 | 3/2015 | Garidel et al. |
| 2015/0259404 | A1 | 9/2015 | Barbour et al. |
| 2016/0251416 | A1 | 9/2016 | Saldanha et al. |
| 2018/0016329 | A1 | 1/2018 | Saldanha et al. |
| 2018/0201669 | A1 | 7/2018 | Saldanha et al. |

(Continued)

FOREIGN PATENT DOCUMENTS

| | | |
|---|---|---|
| EP | 2234600 B1 | 8/2014 |
| JP | H4-217630 | 8/1992 |
| JP | 2000-510813 | 8/2000 |

(Continued)

OTHER PUBLICATIONS

Daugherty, et al., "Formulation and Delivery Issues for Monoclonal Antibody Therapeutics," *Advanced Drug Delivery Reviews*, 58(5-6):686-42 (2006) with permission Elsevier.
EP 12844433.8 European Search Report dated Feb. 17, 2015.
EP 137400871.2 European Search Report dated Jun. 3, 2015.
EP 13845625.6 European Extended Search Report dated Jul. 18, 2016.
LED Association, Inc. 2013, "Incidence of lewy body dementias in a general population", http://222.lbda.org.
Nasstrom, et al., "Antibodies against Alpha-synuclein Reduce Oligomerization in Living Cells," *PloS ONE*, vol. 6, Issue 10, e27230 (Oct. 2011).
PCT/IB2014/062806 International Search Report and Written Opinion of the International Searching Authority dated Apr. 24, 2015.
PCT/IB2014/062806 Invitation to Pay Additional Fees and Where Applicable Protest Fee dated Oct. 29, 2014.

(Continued)

*Primary Examiner* — Yunsoo Kim
(74) *Attorney, Agent, or Firm* — Alston & Bird LLP

(57) ABSTRACT

The invention provides antibody formulations and methods useful for prophylaxis or treatment of synucleinopathies, including Parkinson's disease.

23 Claims, 5 Drawing Sheets
Specification includes a Sequence Listing.

(56) References Cited

U.S. PATENT DOCUMENTS

2019/0153080 A1   5/2019   Saldanha et al.

FOREIGN PATENT DOCUMENTS

| JP | 2008-520551 | 6/2008 |
|---|---|---|
| JP | 2013-5000976 | 1/2013 |
| JP | 2013-504540 | 2/2013 |
| JP | 2013-521769 | 6/2013 |
| JP | 2014-522843 | 9/2014 |
| JP | 2011-246484 | 12/2014 |
| WO | WO 2004/039234 A2 | 5/2004 |
| WO | WO 2004/041067 | 5/2004 |
| WO | WO 2005/47860 A2 | 5/2005 |
| WO | WO 2007/011907 A2 | 1/2007 |
| WO | WO 2008/011348 A2 | 1/2008 |
| WO | WO 2008/103473 A2 | 8/2008 |
| WO | WO 2008/116103 A2 | 9/2008 |
| WO | WO 2010/069603 A1 | 6/2010 |
| WO | WO 2011/090720 A2 | 7/2011 |
| WO | WO 2011/107544 A1 | 9/2011 |
| WO | WO 2011/127324 A2 | 10/2011 |
| WO | WO 2011/155607 A1 | 12/2011 |
| WO | WO 2011/156238 A1 | 12/2011 |
| WO | WO 2012/009631 A1 | 1/2012 |
| WO | WO 2012/160536 A1 | 11/2012 |
| WO | WO 2012/177997 A1 | 12/2012 |
| WO | WO 2013/063516 A1 | 5/2013 |
| WO | WO 2013/066866 A1 | 5/2013 |
| WO | WO 2013/112945 A1 | 8/2013 |
| WO | WO 2014/033074 A1 | 3/2014 |
| WO | WO 2014/039234 A2 | 4/2014 |
| WO | WO 2015/001504 A2 | 1/2015 |
| WO | WO 2015/155694 A1 | 10/2015 |

OTHER PUBLICATIONS

PCT/IB2015/052524 Search Report and Written Opinion dated Jul. 3, 2015.
PCT/US2013/023307 International Preliminary Report on Patentability and Written Opinion dated Jul. 29, 2014.
U.S. Appl. No. 14/049,169 Final Office Action and Telephone Interview dated Oct. 2, 2015.
U.S. Appl. No. 14/049,169 Non-Final Office Action dated Feb. 10, 2015.
U.S. Appl. No. 14/049,169 Office Action dated Mar. 30, 2016.
U.S. Appl. No. 14/156,441 Final Office Action dated Jun. 8, 2016.
U.S. Appl. No. 14/322,797 Restriction Requirement dated Aug. 29, 2016.
U.S. Appl. No. 14/340,342 Non-Final Office Action dated Mar. 3, 2015.
U.S. Appl. No. 14/340,555 Non-Final Office Action dated Apr. 8, 2015.
U.S. Appl. No. 12/156,441 Non-Final Office Action dated Nov. 10, 2014.
U.S. Appl. No. 14/049,169 Restriction Requirement dated Jul. 16, 2014.
Wang, "Advances in the production of human monoclonal antibodies," Antibody Technology Journal, 1: 1-4 (2011).
Wang, et at., "Antibody Structure, Instability, and Formulation", Journal of Pharmaceutical Sciences, vol. 96:1 pp. 1-26 (Jan. 2007).
Wang, W., "Instability, stabilization, and formulation of liquid protein pharmaceuticals," Int. J. Pharmaceutics, 185(2):129-188 (1999).
Warne, et al., "Development of high concentration protein biopharmaceuticals: The use of platform approaches in formulation development," European Journal of Pharmaceutics and Biopharmaceutics, 78:208-212 (2011).
Choi, et al., "Fine epitope mapping of monoclonal antibodies specific to human alpha-synuclein," Neurosci Lett., 17;397(1-2):53-58 (2006) Abstract only.
Finlay et al., "Affinity Maturation of a Humanized Rat Antibody for Anti-RAGE Therapy: Comprehensive Mutagenesis Reveals a Hight Level of Mutational Plasticity Both Inside and Outside the Complementarity-Determining Regions", *J.Mol. Biol.*, 388, pp. 541-558, (2009).
Genbank Accession No. 3NFP A, "Chain A, Crystal Structure of the Fab Fragment of Therapeutic Antibody Daclizumab in Complex With II-2ra (cd25) Ectodomain," Oct. 19, 2013.
Genbank Accession No. AAC28255.1, "Immunoglobulin kappa light chain [Mus musculus]," Dec. 15, 1999.
Genbank Accession No. AAF88044.1, "Immunoglobulin heavy chain variable regions [Mus musculus]," Jul. 27, 2000.
Gonzalas, et al., "SDR grafting of a murine antibody using multiple human germine templates to minimize its immunogenicity," Molecular Immunology, 41:863-872 (2004).
Hackett, et al., "Recombinant Mouse-Human Chimeric Antibodies as Calibrators in Immunoassays That Measure Antibodies to *Toxoplasma gondii*," *J. Clin. Microbiol.*, vol. 36, No. 5, pp. 1277-1284 (1998).
Masliah et al., "Effects of α-Synuclein Immunization in a Mouse Model of Parkinson's Disease", Neuron, 46:857-866, (2005).
Masliah et al., "Passive Immunization Reduces Behavioral and Neuropathological Deficits in an Alpha-Synuclein Transgenic Model of Lewy Body Disease",*PLoS ONE*, 6(4):e19338, pp. 1-17, (Apr. 2011).
Mihara, et al., "CTLA4Ig inhibits T cell-dependent B-cell maturation in murine systemic lupus erythematosus," J. Clin. Invest., vol. 106, No. 1, pp. 91-101 (2000).
PCT/US2002/062290 Written Opinion and Search Report dated Jan. 28, 2013.
PCT/US2013/023307 Written Opinion and Search Report dated May 13, 2013.
PCT/US2013/063945 Invitation to Pay Additional Fees dated Feb. 6, 2014.
PCT/US2013/063945 Written Opinion and Search Report dated Apr. 22, 2014.
Yang, et al., "Structural basis of immunosuppression by the therapeutic antibody dachzumab," *Cell Research*, 20:1361-1371 (2010).
Jones et al., "Deimmunization of Monoclonal Antibodies," *Therapeutic Antibodies: Methods and Protocols*, 525:405-423, (2009).
EP 13845625.6 Supplementary European Search Report completed Jul. 7, 2016.
PCT/IB32014/062806 International Preliminary Report on Patentability dated Jan. 5, 2016.
PCT/IB2015/052524 International Preliminary Report on Patentability dated Oct. 12, 2016.
PCT/US2012/062290 International Preliminary Report on Patentability dated Apr. 29, 2014.
PCT/US2013/063945 International Preliminary Report on Patentability dated Apr. 8, 2015.
U.S. Appl. No. 14/049,169 Examiner Initiated Interview Summary dated Feb. 10, 2015.
U.S. Appl. No. 14/049,169 Examiner Initiated Interview Summary dated Oct. 2, 2015.
U.S. Appl. No. 14/049,169 Examiner Initiated Interview Summary dated Nov. 1, 2016.
U.S. Appl. No. 14/049,169 Notice of Allowance dated Nov. 1, 2016.
U.S. Appl. No. 14/156,441 Examiner Initiated Interview Summary dated Nov. 10, 2014.
U.S. Appl. No. 14/156,441 Notice of Allowance dated Sep. 20, 2016.
U.S. Appl. No. 14/937,792 Examiner Initiated Interview Summary dated Feb. 2, 2017.
U.S. Appl. No. 14/937,792 Examiner Initiated Interview Summary dated Aug. 30, 2016.
U.S. Appl. No. 14/937,792 Non-Final Office Action dated Aug. 30, 2016.
U.S. Appl. No. 14/937,792 Notice of Allowance dated Feb. 2, 2017.
Zhang et al., "Conformation-dependent scFv antibodies specifically recognize the oligomers assembled from various amyloids and show colocalization of amyloid fibrils with oligomers in patients with amyloidoses," Biochimica et Biophysica Acta (BBA)—Protein & Proteomics, 1814(2):1703-1712, (2011).
Roche Data Sheet, "Herceptin 140625" Prepared Jun. 25, 2014.
Xolair, "Highlights of Prescribing Information", Genentech, Inc. (2003).

(56) References Cited

OTHER PUBLICATIONS

U.S. Appl. No. 15/387,580 Notice of Allowance dated Sep. 28, 2017.
U.S. Appl. No. 15/429,962 Non-Final Office Action dated Sep. 22, 2017.
Mahler, et al., "Trends n Formulation and Drug Delivery for Antibodies", Process Scale Purification of Antibodies, Second Edition, Edited by Uwe Gottschalk, 2017 John Wiley & Sons, Inc. Published 2017 by John Wiley & Sons, Inc.
U.S. Appl. No. 15/429,962 Notice of Allowance and Interview Summary dated May 21, 2018.
AMGEN, Inc., Blincyto® (blinatumomab) Highlights of Prescribing Information and Full Prescribing Information revised May 2018.
U.S. Appl. No. 15/587,255 Notice of Allowance and Examiner Initiated Interview Summary dated Jun. 27, 2018.
U.S. Appl. No. 15/857,104 Non-Final Office Action dated Jul. 23, 2018.
EP 18155441.1 Extended European Search Report dated Jun. 18, 2018.
U.S. Appl. No. 15/857,104 Notice of Allowance dated Jan. 29, 2019.
U.S. Appl. No. 16/107,949 Notice of Allowance and Interview Summary dated Jan. 9, 2019.
U.S. Appl. No. 15/387,580, filed Dec. 21, 2016.
U.S. Appl. No. 14/937,792, filed Nov. 10, 2015; published as US 2016-0251416 on Sep. 1, 2016.
U.S. Appl. No. 14/049,169, filed Oct. 8, 2013; published as US 2014/0127131 on May 8, 2014.
U.S. Appl. No. 15/429,962, filed Feb. 10, 2017.
U.S. Appl. No. 15/387,580, filed Dec. 21, 2016; published as US 2017-0240621 on Aug. 24, 2017.
U.S. Appl. No. 15/429,962, filed Feb. 10, 2017; published as US 2017-0152310 on Jun. 1, 2017.
U.S. Appl. No. 15/587,255, filed May 4, 2017.
U.S. Appl. No. 61/977,042, filed Apr. 8, 2004.
U.S. Appl. No. 62/023,373, filed Jul. 11, 2004.
U.S. Appl. No. 16/144,923, filed Sep. 27, 2018.
U.S. Appl. No. 16/107,949, filed Aug. 21, 2018.
U.S. Appl. No. 13/662,261, filed Oct. 26, 2012; issued as U.S. Pat. No. 8,609,820 on Dec. 17, 2013.
U.S. Appl. No. 13/750,983, filed Jan. 25, 2013; issued as U.S. Pat. No. 8,790,644 on Jul. 29, 2014.
U.S. Appl. No. 14/049,169, filed Oct. 8, 2013; issued as U.S. Pat. No. 9,605,056 on Mar. 28, 2017.
U.S. Appl. No. 14/156,441, filed Jan. 15, 2014; issued as U.S. Pat. No. 9,556,259 on Jan. 31, 2017.
U.S. Appl. No. 14/322,797, filed Jul. 2, 2014; published as US 2015/0079074 on Mar. 16, 2015.
U.S. Appl. No. 14/340,342, filed Jul. 24, 2014; issued as U.S. Pat. No. 9,234,031 on Jan. 12, 2016.
U.S. Appl. No. 14/340,355, filed Jul. 24, 2014; issued as U.S. Pat. No. 9,217,030 on Dec. 22, 2015.
U.S. Appl. No. 14/937,792, filed Nov. 10, 2015; issued as U.S. Pat. No. 9,670,273 on Jun. 6, 2017.
U.S. Appl. No. 15/387,580, filed Dec. 21, 2016; issued as U.S. Pat. No. 9,884,906 on Feb. 6, 2018.
U.S. Appl. No. 15/429,962, filed Feb. 10, 2017; issued as U.S. Pat. No. 10,081,674 on Sep. 25, 2018.
U.S. Appl. No. 15/587,255, filed May 4, 2017; issued as U.S. Pat. No. 10,118,960 on Nov. 6, 2018.
U.S. Appl. No. 15/857,104, filed Dec. 28, 2017; published as US 2018/0201669 on Jul. 19, 2018.
U.S. Appl. No. 16/107,949, filed Aug. 21, 2018; issued as U.S. Pat. No. 10,301,382 on May 28, 2019.
U.S. Appl. No. 16/144,923, filed Sep. 27, 2018; published as US 2019/0153080 on May 23, 2019.
PCT/US2012/062290 filed Oct. 26, 2012; published as WO 2013/063516 on May 2, 2013.
U.S. Appl. No. 61/553,131, filed Oct. 28, 2011.
U.S. Appl. No. 61/711,208, filed Oct. 8, 2012.
PCT/US2013/023307 filed Jan. 25, 2013; published as WO 2013/112945 on Aug. 1, 2013.
U.S. Appl. No. 61/591,835, filed Jan. 27, 2012.
U.S. Appl. No. 61/711,207, filed Oct. 8, 2012.
U.S. Appl. No. 61/436,999, filed Jan. 27, 2011.
U.S. Appl. No. 61/450,603, filed Mar. 8, 2011.
PCT/US2013/063945 filed Oct. 8, 2013; published as WO 2014/058924 on Apr. 17, 2014.
U.S. Appl. No. 61/711,204, filed Oct. 8, 2012.
U.S. Appl. No. 61/719,281, filed Oct. 26, 2012.
U.S. Appl. No. 61/840,432, filed Jun. 27, 2013.
U.S. Appl. No. 61/872,366, filed Aug. 30, 2013.
U.S. Appl. No. 14/434,089, filed Apr. 7, 2015; published as US 2015/0259404 on Sep. 17, 2015.
PCT/IB2014/062806 filed Jul. 3, 2014; published as WO 2015/001504 on Jan. 8, 2015.
U.S. Appl. No. 61/843,011, filed Jul. 4, 2013.
U.S. Appl. No. 61/979,886, filed Apr. 15, 2014.
PCT/IB2015/052524 filed Apr. 8, 2015; published as WO/2015/155694 on Oct. 15, 2015.
U.S. Appl. No. 61/977,039, filed Apr. 8, 2014.
U.S. Appl. No. 61/977,042, filed Apr. 8, 2014.
U.S. Appl. No. 62/023,373, filed Jul. 11, 2014.

\* cited by examiner

SEQUENCE LISTING

```
<160> NUMBER OF SEQ ID NOS: 33

<210> SEQ ID NO 1
<211> LENGTH: 113
<212> TYPE: PRT
<213> ORGANISM: Artificial Sequence
<220> FEATURE:
<223> OTHER INFORMATION: Synthesized

<400> SEQUENCE: 1

Asp Ile Val Met Ser Gln Ser Pro Ser Ser Leu Ala Val Ser Val Gly
1               5                   10                  15

Glu Lys Val Thr Met Ser Cys Lys Ser Ile Gln Thr Leu Leu Tyr Ser
                20                  25                  30

Ser Asn Gln Lys Asn Tyr Leu Ala Trp Phe Gln Lys Pro Gly Gln
            35                  40                  45

Ser Pro Lys Leu Leu Ile Tyr Trp Ala Ser Ile Arg Lys Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110

Lys

<210> SEQ ID NO 2
<211> LENGTH: 107
<212> TYPE: PRT
<213> ORGANISM: Artificial Sequence
<220> FEATURE:
<223> OTHER INFORMATION: Synthesized

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
```

```
65                  70                  75                  80
Glu Asp Phe Ala Thr Tyr Tyr Cys Gln Gln Ser Tyr Ser Thr Pro Leu
                85                  90                  95
Thr Phe Gly Gly Gly Thr Lys Leu Glu Ile Lys
                100                 105

<210> SEQ ID NO 3
<211> LENGTH: 113
<212> TYPE: PRT
<213> ORGANISM: Artificial Sequence
<220> FEATURE:
<223> OTHER INFORMATION: Synthesized

<400> SEQUENCE: 3

Asp Ile Gln Met Thr Gln Ser Pro Ser Ser Leu Ser Ala Ser Val Gly
1               5                   10                  15
Asp Arg Val Thr Ile Thr Cys Lys Ser Ile Gln Thr Leu Leu Tyr Ser
                20                  25                  30
Ser Asn Gln Lys Asn Tyr Leu Ala Trp Phe Gln Gln Lys Pro Gly Lys
            35                  40                  45
Ala Pro Lys Leu Leu Ile Tyr Trp Ala Ser Ile Arg Lys Ser Gly Val
        50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Ser Tyr Pro Leu Thr Phe Gly Gly Gly Thr Lys Leu Glu Ile
                100                 105                 110
Lys

<210> SEQ ID NO 4
<211> LENGTH: 113
<212> TYPE: PRT
<213> ORGANISM: Artificial Sequence
<220> FEATURE:
<223> OTHER INFORMATION: Synthesized

<400> SEQUENCE: 4

Asp Ile Gln Met Thr Gln Ser Pro Ser Ser Leu Ser Ala Ser Val Gly
1               5                   10                  15
Asp Arg Val Thr Ile Thr Cys Lys Ser Ile Gln Thr Leu Leu Tyr Ser
                20                  25                  30
Ser Asn Gln Lys Asn Tyr Leu Ala Trp Tyr Gln Gln Lys Pro Gly Lys
            35                  40                  45
Ala Pro Lys Leu Leu Ile Tyr Trp Ala Ser Ile Arg Lys Ser Gly Val
        50                  55                  60
Pro Ser Arg Phe Ser Gly Ser Gly Ser Gly Thr Asp Phe Thr Leu Thr
65                  70                  75                  80
Ile Ser Ser Leu Gln Pro Glu Asp Phe Ala Thr Tyr Tyr Cys Gln Gln
                85                  90                  95
Tyr Tyr Ser Tyr Pro Leu Thr Phe Gly Gly Gly Thr Lys Leu Glu Ile
                100                 105                 110
Lys

<210> SEQ ID NO 5
<211> LENGTH: 113
<212> TYPE: PRT
<213> ORGANISM: Artificial Sequence
```

```
<220> FEATURE:
<223> OTHER INFORMATION: Synthesized

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
            20                  25                  30

Ser Asn Gln Lys Asn Tyr Leu Ala Trp Phe Gln Gln Lys Pro Gly Lys
        35                  40                  45

Ala Pro Lys Leu Leu Ile Tyr Trp Ala Ser Ile Arg Lys Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Leu Ala Thr Tyr Tyr Cys Gln Gln
                85                  90                  95

Tyr Tyr Ser Tyr Pro Leu Thr Phe Gly Gly Gly Thr Lys Leu Glu Ile
            100                 105                 110

Lys

<210> SEQ ID NO 6
<211> LENGTH: 116
<212> TYPE: PRT
<213> ORGANISM: Artificial Sequence
<220> FEATURE:
<223> OTHER INFORMATION: Synthesized

<400> SEQUENCE: 6

Glu Val Lys Leu Val Glu Ser Gly Gly Gly Leu Val Lys Pro Gly Ala
1               5                   10                  15

Ser Leu Lys Leu Ser Cys Ala Ala Ser Gly Phe Thr Phe Ser Asn Tyr
            20                  25                  30

Gly Met Ser Trp Val Arg Gln Thr Ser Asp Lys Arg Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Glu Asp Ala Lys Asn Thr Leu Tyr
65                  70                  75                  80

Leu Gln Met Ser Ser Leu Arg Ser Glu Asp Thr Ala Leu Tyr Tyr Cys
                85                  90                  95

Ser Arg Gly Gly Ala Gly Ile Asp Tyr Trp Gly Gln Gly Thr Thr Leu
            100                 105                 110

Thr Val Ser Ser
        115

<210> SEQ ID NO 7
<211> LENGTH: 116
<212> TYPE: PRT
<213> ORGANISM: Artificial Sequence
<220> FEATURE:
<223> OTHER INFORMATION: Synthesized

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
```

```
                35                  40                  45
Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Ser Ser Asp Met Asp Tyr Trp Gly Gln Gly Thr Leu Val
            100                 105                 110

Thr Val Ser Ser
            115

<210> SEQ ID NO 8
<211> LENGTH: 116
<212> TYPE: PRT
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Gly Met Ser Trp Val Arg Gln Ala Pro Gly Lys Gly Leu Glu Trp Val
         35                  40                  45

Ala Ser Ile Ser Ser Gly Gly Ser Thr Tyr Tyr Pro Asp Asn Val
     50                  55                  60

Lys Gly Arg Phe Thr Ile Ser Arg Asp Asp Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ser Arg Gly Gly Ala Gly Ile Asp Tyr Trp Gly Gln Gly Thr Leu Val
            100                 105                 110

Thr Val Ser Ser
            115

<210> SEQ ID NO 9
<211> LENGTH: 116
<212> TYPE: PRT
<213> ORGANISM: Artificial Sequence
<220> FEATURE:
<223> OTHER INFORMATION: Synthesized

<400> SEQUENCE: 9

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
             20                  25                  30

Gly Met Ser Trp Val Arg Gln Ala Pro Gly Lys Gly Leu Glu Trp Val
         35                  40                  45

Ala Ser Ile Ser Ser Gly Gly Ser Thr Tyr Tyr Pro Asp Asn Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95
```

```
Ser Arg Gly Gly Ala Gly Ile Asp Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthesized

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthesized

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser
        115

<210> SEQ ID NO 12
<211> LENGTH: 140
<212> TYPE: PRT
<213> ORGANISM: Artificial Sequence
```

```
<220> FEATURE:
<223> OTHER INFORMATION: Synthesized

<400> SEQUENCE: 12

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
            20                  25                  30

Thr Lys Glu Gly Val Leu Tyr Val Gly Ser Lys Thr Lys Glu Gly Val
        35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
            85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
        130                 135                 140

<210> SEQ ID NO 13
<211> LENGTH: 107
<212> TYPE: PRT
<213> ORGANISM: Artificial Sequence
<220> FEATURE:
<223> OTHER INFORMATION: Synthesized

<400> SEQUENCE: 13

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
            100                 105

<210> SEQ ID NO 14
<211> LENGTH: 330
<212> TYPE: PRT
<213> ORGANISM: Artificial Sequence
<220> FEATURE:
<223> OTHER INFORMATION: Synthesized

<400> SEQUENCE: 14

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Val Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 15
<211> LENGTH: 339
<212> TYPE: DNA
<213> ORGANISM: Artificial Sequence
<220> FEATURE:
<223> OTHER INFORMATION: Synthesized

<400> SEQUENCE: 15
gacatccaga tgacccagtc cccctcctcc ctgtccgcct ccgtgggcga ccgcgtgacc     60
atcacctgca gtccatcca gaccctgctg tactcctcca accagaagaa ctacctggcc    120
tggttccagc agaagcccgg caaggccccc aagctgctga tctactgggc ctccatccgc    180
aagtccggcg tgccctcccg cttctccggc tccggctccg gcaccgactt caccctgacc    240
atctcctccc tgcagcccga ggacttcgcc acctactact gccagcagta ctactcctac    300
cccctgacct tcggcggcgg caccaagctg gagatcaag                           339
```

<210> SEQ ID NO 16
<211> LENGTH: 339
<212> TYPE: DNA
<213> ORGANISM: Artificial Sequence
<220> FEATURE:
<223> OTHER INFORMATION: Synthesized

<400> SEQUENCE: 16

```
gacatccaga tgacccagtc cccctcctcc ctgtccgcct ccgtgggcga ccgcgtgacc        60
atcacctgca agtccatcca gaccctgctg tactcctcca accagaagaa ctacctggcc       120
tggtaccagc agaagcccgg caaggccccc aagctgctga tctactgggc ctccatccgc       180
aagtccggcg tgccctcccg cttctccggc tccggctccg gcaccgactt cacccctgacc     240 atctcctccc tgcagcccga ggacttcgcc acctactact gccagcagta ctactcctac       300
cccctgacct cggcggcgg caccaagctg gagatcaag                               339
```

<210> SEQ ID NO 17
<211> LENGTH: 339
<212> TYPE: DNA
<213> ORGANISM: Artificial Sequence
<220> FEATURE:
<223> OTHER INFORMATION: Synthesized

<400> SEQUENCE: 17

```
gacatccaga tgacccagtc cccctcctcc ctgtccgcct ccgtgggcga ccgcgtgacc        60
atcacctgca agtccatcca gaccctgctg tactcctcca accagaagaa ctacctggcc       120
tggttccagc agaagcccgg caaggccccc aagctgctga tctactgggc ctccatccgc       180
aagtccggcg tgccctcccg cttctccggc tccggctccg gcaccgactt cacccctgacc     240 atctcctccc tgcagcccga ggacctggcc acctactact gccagcagta ctactcctac       300
cccctgacct cggcggcgg caccaagctg gagatcaag                               339
```

<210> SEQ ID NO 18
<211> LENGTH: 348
<212> TYPE: DNA
<213> ORGANISM: Artificial Sequence
<220> FEATURE:
<223> OTHER INFORMATION: Synthesized

<400> SEQUENCE: 18

```
gaggtgcagc tggtggagtc cggcggcggc ctggtgcagc ccggcggctc cctgcgcctg        60
tcctgcgccg cctccggctt caccttctcc aactacggca tgtcctgggt cgcccaggcc       120
cccggcaagg gcctggagtg ggtggcctcc atctcctccg gcggcggctc cacctactac       180
cccgacaacg tgaagggccg cttcaccatc tcccgcgacg acgccaagaa ctccctgtac       240
ctgcagatga actccctgcg cgccgaggac accgccgtgt actactgctc ccgcggcggc       300
gccggcatcg actactgggg ccagggcacc ctggtgaccg tgtcctcc                    348
```

<210> SEQ ID NO 19
<211> LENGTH: 348
<212> TYPE: DNA
<213> ORGANISM: Artificial Sequence
<220> FEATURE:
<223> OTHER INFORMATION: Synthesized

<400> SEQUENCE: 19

```
gaggtgcagc tggtggagtc cggcggcggc ctggtgcagc ccggcggctc cctgcgcctg        60
tcctgcgccg cctccggctt caccttctcc aactacggca tgtcctgggt cgcccaggcc       120
```

```
cccggcaagg gcctggagtg ggtggcctcc atctcctccg gcggcggctc cacctactac      180
cccgacaacg tgaagggccg cttcaccatc tcccgcgaca cgccaagaa ctccctgtac       240 ctgcagatga actccctgcg cgccgaggac accgccgtgt actactgctc ccgcggcggc      300
gccggcatcg actactgggg ccagggcacc ctggtgaccg tgtcctcc                   348
```

<210> SEQ ID NO 20
<211> LENGTH: 348
<212> TYPE: DNA
<213> ORGANISM: Artificial Sequence
<220> FEATURE:
<223> OTHER INFORMATION: Synthesized

<400> SEQUENCE: 20

```
gaggtgcagc tggtggagtc cggcggcggc ctggtgcagc ccggcggctc cctgcgcctg      60
tcctgcgccg cctccggctt caccttctcc aactacggca tgtcctgggt cgccaggcc       120 cccggcaagg gcctggagtg ggtggcctcc atctcctccg gcggcggctc cacctactac      180
cccgacaacg tgaagggccg cttcaccatc tcccgcgacg acgccaagaa ctccctgtac      240
ctgcagatga actccctgcg cgccgaggac accgccgtgt actactgcgc ccgcggcggc      300
gccggcatcg actactgggg ccagggcacc ctggtgaccg tgtcctcc                   348
```

<210> SEQ ID NO 21
<211> LENGTH: 348
<212> TYPE: DNA
<213> ORGANISM: Artificial Sequence
<220> FEATURE:
<223> OTHER INFORMATION: Synthesized

<400> SEQUENCE: 21

```
gaggtgcagc tggtggagtc cggcggcggc ctggtgcagc ccggcggctc cctgcgcctg      60
tcctgcgccg cctccggctt caccttctcc aactacggca tgtcctgggt cgccaggcc       120 cccggcaagg gcctggagtg ggtggcctcc atctcctccg gcggcggctc cacctactac      180
cccgacaacg tgaagggccg cttcaccatc tcccgcgaca cgccaagaa ctccctgtac       240 ctgcagatga actccctgcg cgccgaggac accgccgtgt actactgcgc ccgcggcggc      300
gccggcatcg actactgggg ccagggcacc ctggtgaccg tgtcctcc                   348
```

<210> SEQ ID NO 22
<211> LENGTH: 22
<212> TYPE: PRT
<213> ORGANISM: Artificial Sequence
<220> FEATURE:
<223> OTHER INFORMATION: Synthesized

<400> SEQUENCE: 22

Met Asp Met Arg Val Pro Ala Gln Leu Leu Gly Leu Leu Met Leu Trp
1               5                   10                  15

Val Ser Gly Ser Ser Gly
            20

<210> SEQ ID NO 23
<211> LENGTH: 66
<212> TYPE: DNA
<213> ORGANISM: Artificial Sequence
<220> FEATURE:
<223> OTHER INFORMATION: Synthesized

<400> SEQUENCE: 23

```
atggacatgc gcgtgcccgc ccagctgctg ggcctgctga tgctgtgggt gtccggctcc    60
tccggc                                                                66
```

<210> SEQ ID NO 24
<211> LENGTH: 19
<212> TYPE: PRT
<213> ORGANISM: Artificial Sequence
<220> FEATURE:
<223> OTHER INFORMATION: Synthesized

<400> SEQUENCE: 24

Met Glu Phe Gly Leu Ser Trp Leu Phe Leu Val Ala Ile Leu Lys Gly
1               5                   10                  15

Val Gln Cys

<210> SEQ ID NO 25
<211> LENGTH: 57
<212> TYPE: DNA
<213> ORGANISM: Artificial Sequence
<220> FEATURE:
<223> OTHER INFORMATION: Synthesized

<400> SEQUENCE: 25

```
atggagttcg gcctgtcctg gctgttcctg gtggccatcc tgaagggcgt gcagtgc       57
```

<210> SEQ ID NO 26
<211> LENGTH: 113
<212> TYPE: PRT
<213> ORGANISM: Artificial Sequence
<220> FEATURE:
<223> OTHER INFORMATION: Synthesized
<220> FEATURE:
<221> NAME/KEY: VARIANT
<222> LOCATION: 42
<223> OTHER INFORMATION: Xaa = Y or F
<220> FEATURE:
<221> NAME/KEY: VARIANT
<222> LOCATION: 89
<223> OTHER INFORMATION: Xaa = F or L

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Lys Ser Ile Gln Thr Leu Leu Tyr Ser
                20                  25                  30

Ser Asn Gln Lys Asn Tyr Leu Ala Trp Xaa Gln Gln Lys Pro Gly Lys
            35                  40                  45

Ala Pro Lys Leu Leu Ile Tyr Trp Ala Ser Ile Arg Lys Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Xaa Ala Thr Tyr Tyr Cys Gln Gln
                85                  90                  95

Tyr Tyr Ser Tyr Pro Leu Thr Phe Gly Gly Gly Thr Lys Leu Glu Ile
                100                 105                 110

Lys

<210> SEQ ID NO 27
<211> LENGTH: 116
<212> TYPE: PRT
<213> ORGANISM: Artificial Sequence
<220> FEATURE:
<223> OTHER INFORMATION: Synthesized

```
<220> FEATURE:
<221> NAME/KEY: VARIANT
<222> LOCATION: 74
<223> OTHER INFORMATION: Xaa = N or D
<220> FEATURE:
<221> NAME/KEY: VARIANT
<222> LOCATION: 97
<223> OTHER INFORMATION: Xaa = A or S

<400> SEQUENCE: 27

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Xaa Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Xaa Arg Gly Gly Ala Gly Ile Asp Tyr Trp Gly Gln Gly Thr Leu Val
            100                 105                 110

Thr Val Ser Ser
        115

<210> SEQ ID NO 28
<211> LENGTH: 106
<212> TYPE: PRT
<213> ORGANISM: Artificial Sequence
<220> FEATURE:
<223> OTHER INFORMATION: Synthesized

<400> SEQUENCE: 28

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 29
<211> LENGTH: 220
<212> TYPE: PRT
<213> ORGANISM: Artificial Sequence
<220> FEATURE:
<223> OTHER INFORMATION: Synthesized

<400> SEQUENCE: 29

Asp Ile Gln Met Thr Gln Ser Pro Ser Ser Leu Ser Ala Ser Val Gly
1               5                   10                  15
```

```
Asp Arg Val Thr Ile Thr Cys Lys Ser Ile Gln Thr Leu Leu Tyr Ser
             20                  25                  30

Ser Asn Gln Lys Asn Tyr Leu Ala Trp Phe Gln Gln Lys Pro Gly Lys
         35                  40                  45

Ala Pro Lys Leu Leu Ile Tyr Trp Ala Ser Ile Arg Lys Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Leu Ala Thr Tyr Tyr Cys Gln Gln
                 85                  90                  95

Tyr Tyr Ser Tyr Pro Leu Thr Phe Gly Gly Gly Thr Lys Leu Glu Ile
             100                 105                 110

Lys Arg Thr Val Ala Ala Pro Ser Val Phe Ile Phe Pro Pro Ser Asp
         115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                 165                 170                 175

Ser Thr Tyr Ser Leu Ser Ser Thr Leu Thr Leu Ser Lys Ala Asp Tyr
             180                 185                 190

Glu Lys His Lys Val Tyr Ala Cys Glu Val Thr His Gln Gly Leu Ser
         195                 200                 205

Ser Pro Val Thr Lys Ser Phe Asn Arg Gly Glu Cys
210                 215                 220

<210> SEQ ID NO 30
<211> LENGTH: 219
<212> TYPE: PRT
<213> ORGANISM: Artificial Sequence
<220> FEATURE:
<223> OTHER INFORMATION: Synthesized

<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Lys Ser Ile Gln Thr Leu Leu Tyr Ser
             20                  25                  30

Ser Asn Gln Lys Asn Tyr Leu Ala Trp Phe Gln Gln Lys Pro Gly Lys
         35                  40                  45

Ala Pro Lys Leu Leu Ile Tyr Trp Ala Ser Ile Arg Lys Ser Gly Val
 50                  55                  60

Pro Ser Arg Phe Ser Gly Ser Gly Ser Gly Thr Asp Phe Thr Leu Thr
 65                  70                  75                  80

Ile Ser Ser Leu Gln Pro Glu Asp Leu Ala Thr Tyr Tyr Cys Gln Gln
                 85                  90                  95

Tyr Tyr Ser Tyr Pro Leu Thr Phe Gly Gly Gly Thr Lys Leu Glu Ile
             100                 105                 110

Lys Thr Val Ala Ala Pro Ser Val Phe Ile Phe Pro Pro Ser Asp Glu
         115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 446
<212> TYPE: PRT
<213> ORGANISM: Artificial Sequence
<220> FEATURE:
<223> OTHER INFORMATION: Synthesized

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Val Lys Thr
        275                 280                 285

Lys Pro Arg Glu Glu Gln Tyr Asn Ser Thr Tyr Arg Val Val Ser Val
    290                 295                 300

```
Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 32
<211> LENGTH: 446
<212> TYPE: PRT
<213> ORGANISM: Artificial Sequence
<220> FEATURE:
<223> OTHER INFORMATION: Synthesized

<400> SEQUENCE: 32

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Gly Met Ser Trp Val Arg Gln Ala Pro Gly Lys Gly Leu Glu Trp Val
        35                  40                  45

Ala Ser Ile Ser Ser Gly Gly Gly Ser Thr Tyr Tyr Pro Asp Asn Val
    50                  55                  60

Lys Gly Arg Phe Thr Ile Ser Arg Asp Asp Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Ala Gly Ile Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220
```

```
Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
        260                 265                 270

Lys Phe Asn Trp Tyr Val Asp Gly Val Glu Val His Asn Ala Lys Thr
    275                 280                 285

Lys Pro Arg Glu Glu Gln Tyr Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
            325                 330                 335

Lys Ala Lys Gly Gln Pro Arg Glu Pro Gln Val Tyr Thr Leu Pro Pro
        340                 345                 350

Ser Arg Glu Glu Met Thr Lys Asn Gln Val Ser Leu Thr Cys Leu Val
    355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
            405                 410                 415

Gln Gln Gly Asn Val Phe Ser Cys Ser Val Met His Glu Ala Leu His
        420                 425                 430

Asn His Tyr Thr Gln Lys Ser Leu Ser Leu Ser Pro Gly Lys
    435                 440                 445

<210> SEQ ID NO 33
<211> LENGTH: 330
<212> TYPE: PRT
<213> ORGANISM: Artificial Sequence
<220> FEATURE:
<223> OTHER INFORMATION: Synthesized

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140
```

```
Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330
```

ANTIBODY FORMULATIONS AND METHODS

CROSS REFERENCE TO RELATED APPLICATIONS

This application claims the benefit of U.S. Provisional Patent Application No. 61/843,011, filed Jul. 4, 2013, and U.S. Provisional Patent Application No. 61/979,886, filed Apr. 15, 2014, both of which are incorporated by reference in their entirety for all purposes.

REFERENCE TO A SEQUENCE LISTING

The Sequence Listing written in file 446074SEQLIST.txt, created on Jul. 1, 2014, for "Antibody Formulations And Methods" is 37.9 kilobytes. The information contained in this file is hereby incorporated by reference.

BACKGROUND

Synucleinopathies, also known as Lewy body diseases (LBDs), are characterized by degeneration of the dopaminergic system, motor alterations, cognitive impairment, and formation of Lewy bodies (LBs) and/or Lewy neurites. (McKeith et al., Neurology (1996) 47:1113-24). Synucleinopathies include Parkinson's disease (including idiopathic Parkinson's disease), Diffuse Lewy Body Disease (DLBD) also known as Dementia with Lewy Bodies (DLB), Lewy body variant of Alzheimer's disease (LBV), Combined Alzheimer's and Parkinson disease, pure autonomic failure and multiple system atrophy (MSA; e.g., Olivopontocerebellar Atrophy, Striatonigral Degeneration and Shy-Drager Syndrome). Several nonmotor signs and symptoms are thought to be harbingers for synucleinopathies in the prodromal phase of the diseases (i.e., the presymptomatic, subclinical, preclinical, or premotor period). Such early signs include, for example, REM sleep behavior disorder (RBD), loss of smell and constipation (Mahowald et al., Neurology (2010) 75:488-489). Lewy body diseases continue to be a common cause for movement disorders and cognitive deterioration in the aging population (Galasko et al., Arch. Neurol. (1994) 51:888-95).

Alpha-synuclein is part of a large family of proteins including beta- and gamma-synuclein and synoretin. Alpha-synuclein is expressed in the normal state associated with synapses and is believed to play a role in neural plasticity, learning and memory. Several studies have implicated alpha-synuclein with a central role in PD pathogenesis. The protein can aggregate to form insoluble fibrils in pathological conditions. For example, synuclein accumulates in LBs (Spillantini et al., Nature (1997) 388:839-40; Takeda et al., J. Pathol. (1998) 152:367-72; Wakabayashi et al., Neurosci. Lett. (1997) 239:45-8). Mutations in the alpha-synuclein gene co-segregate with rare familial forms of parkinsonism (Kruger et al., Nature Gen. (1998) 18:106-8; Polymeropoulos, et al., Science (1997) 276:2045-7). Over expression of alpha synuclein in transgenic mice (Masliah et al., Science (2000) 287:1265-9) and *Drosophila* (Feany et al., Nature (2000) 404:394-8) mimics several pathological aspects of Lewy body disease. In addition, it has been suggested that soluble oligomers of synuclein may be neurotoxic (Conway K A, et al., Proc Natl Acad Sci USA (2000) 97:571-576; Volles M J, Lansbury P T, Jr Biochemistry (2003) 42:7871-7878). The accumulation of alpha-synuclein with similar morphological and neurological alterations in species and animal models as diverse as humans, mice, and flies suggests that this molecule contributes to the development of Lewy body disease.

SUMMARY OF THE CLAIMED INVENTION

The present invention provides antibody formulations useful for prophylaxis and treatment of synucleinopathy. The invention provides pharmaceutical formulations comprising (a) a chimeric, veneered, or humanized version of antibody 9E4 (ATCC Accession Number PTA-8221), or fragment thereof which specifically competes for binding with 9E4, and/or which is directed to an epitope within amino acid residues 118-126 of alpha-synuclein, wherein the antibody is present at a concentration within the range from about 1 mg/mL to about 100 mg/mL; (b) citrate buffer present at a concentration within the range from about 10 mM to about 30 mM; (c) trehalose present at a concentration within the range from about 210 mM to about 250 mM; and (d) polysorbate 20 present at a concentration within the range from about 0.005% to about 0.05% by weight; wherein the formulation is characterized by a pH within the range from about 5.5 to about 7. Some formulations, for example, comprise an antibody comprising a mature humanized heavy chain variable region at least 90% identical to SEQ ID NO:11 and comprising the three Kabat CDRs of SEQ ID NO:11, and a humanized light chain at least 90% identical to SEQ ID NO:4 and comprising the three Kabat CDRs of SEQ ID NO:4.

In some formulations of the invention, the antibody is present at a concentration within the range from about 5-100 mg/ml, e.g., 5 mg/mL to about 15 mg/mL (e.g., about 10 mg/mL), or present at a concentration within the range from about 25-75 mg/mL (e.g., about 50 mg/mL). In some formulations of the invention, the antibody is present at a concentration within the range from about 36 mg/mL to about 44 mg/mL (e.g., about 40 mg/mL).

In some formulations of the invention, citrate buffer is present at a concentration of about 20 mM.

In some formulations of the invention, trehalose is present at a concentration of about 230 mM.

Prepared as described herein, some representative formulations of the invention (a) are characterized by an osmolality of about 335 mOsm/kg; (b) comprise less than about 10% of the antibody present as an aggregate in the formulation; (c) further comprise a bulking agent; (d) are sterile; and/or (e) are stable on freezing and thawing. Prepared as described herein, some representative formulations of the invention (a) are characterized by an osmolality of about 295 mOsm/kg to about 375 mOsm/kg; (b) comprise less than about 10% or less than about 5% of the antibody present as an aggregate in the formulation; (c) further comprise a bulking agent; (d) are sterile; and/or (e) are stable on freezing and thawing.

In one aspect of the invention, a formulation comprises (a) an antibody comprising a light chain having an amino acid sequence comprising SEQ ID NO: 29 and a heavy chain having an amino acid sequence comprising SEQ ID NO: 31 or 32, with or without C-terminal lysines, wherein the antibody is present at a concentration of about 40 mg/mL; (b) a citrate buffer present at a concentration of about 20 mM; (c) trehalose present at a concentration of about 230 mM; (d) polysorbate 20 present at a concentration of about 0.2 g/L; and (e) a pH of about 6.0.

The pharmaceutical formulation can comprise (a) an antibody, which is antibody 9E4 (ATCC Accession Number PTA-8221) or a chimeric, veneered, or humanized version of antibody 9E4, a fragment thereof which specifically competes for binding with 9E4, and/or a chimeric, veneered, humanized, or human antibody which is directed to an epitope within amino acid residues 118-126 of alpha-synuclein, wherein the antibody is present at a concentration within the range from about 1 mg/mL to about 100 mg/mL; (b) a buffer; (c) a sugar and/or polyol; and (d) a surfactant. In particular examples, the antibody of the disclosed formulations comprises a light chain having an amino acid sequence comprising SEQ ID NO: 29 and a heavy chain having an amino acid sequence comprising SEQ ID NO: 32 with or without the C-terminal lysine.

The antibody formulations can be lyophilized. For example, a representative lyophilized formulation can comprise: (a) a humanized version of antibody 9E4 (ATCC Accession Number PTA-8221) or antigen binding fragment thereof; (b) histidine, citrate, or succinate; (c) trehalose, sucrose, or a mixture of sucrose and mannitol; and (d) polysorbate 20. Lyophilized formulations can have a pH of between about 6 to about 7 when reconstituted, such as pH 6.0 or 6.5 when reconstituted. Lyophilized formulations typically comprise about 40 mg to about 1000 mg of the antibody. Lyophilized formulations typically comprise polysorbate 20 at a concentration within the range from about 0.005% to about 0.05% by weight. Following reconstitution, the lyophilized formulations yield an aqueous solution. For example, the reconstituted aqueous solution can comprise: (a) a humanized version of antibody 9E4 (e.g., an antibody comprising a light chain having an amino acid sequence comprising SEQ ID NO: 29 and a heavy chain having an amino acid sequence comprising any one of SEQ ID NO: 31 or 32, with or without the C-terminal lysine) which is present at a concentration of about 40 mg/mL; (b) a citrate buffer present at a concentration of about 20 mM; (c) trehalose present at a concentration of about 230 mM; (d) polysorbate 20 present at a concentration of about 0.2 g/L; and (e) a pH of about 6.0. A representative lyophilized formulation comprises about 200 mg of the antibody.

Also provided are nucleic acids encoding antibodies used to prepare the disclosed formulations. For example, such nucleic acids include nucleic acids comprising nucleotide sequences encoding an antibody light chain of SEQ ID NO: 29, and nucleic acids comprising nucleotide sequences encoding an antibody heavy chain of SEQ ID NO: 32. For example, the nucleotide sequence set forth as SEQ ID NO: 17 encodes the humanized 9E4 light chain variable region component of SEQ ID NO: 29. As another example, the nucleotide sequence set forth as SEQ ID NO: 20 encodes the humanized 9E4 heavy chain variable region component of SEQ ID NO: 32.

For the production of antibodies, the disclosed nucleic acids may be included in a vector, either singly or in combination (e.g., a combination of a nucleic acid encoding a humanized 9E4 light chain and a nucleic acid encoding a humanized 9E4 heavy chain). For example, a vector can comprise a nucleic acid comprising a nucleotide sequence encoding any one of SEQ ID NOs: 15-17; a nucleic acid comprising the nucleotide sequence of any one of SEQ ID NOs: 18-20, or combinations thereof. Representative vectors of the invention include (a) a vector comprising a nucleic acid sequence encoding a humanized 9E4 light chain set forth as SEQ ID NO: 29 and a humanized 9E4 heavy chain set forth as SEQ ID NO: 31; and (b) a vector comprising a nucleic acid encoding the amino acid sequence of SEQ ID NO: 29 and a nucleic acid encoding the amino acid sequence of SEQ ID NO: 32.

Also provided are host cells (e.g., CHO cells) having stably incorporated into their genomes one or more of the nucleic acids disclosed herein. For example, a host cell can comprise in its genome a stably integrated nucleic acid comprising a nucleotide sequence encoding any one of SEQ ID NOs: 15-17; a stably integrated nucleic acid comprising the nucleotide sequence of any one of SEQ ID NOs: 18-20, or combinations thereof. Representative host cells of the invention include: (a) host cells comprising a nucleic acid sequence encoding a humanized 9E4 light chain set forth as SEQ ID NO: 29 and a humanized 9E4 heavy chain set forth as SEQ ID NO: 31; and (b) host cells comprising a nucleic acid having the nucleotide sequence of SEQ ID NO: 29 and a nucleic acid having the nucleotide sequence of SEQ ID NO: 32.

The present invention also provides methods of preparing pharmaceutical formulations. In one aspect of the invention, such a method comprises: (a) culturing mammalian cells having stably incorporated into their genome nucleic acids encoding the light and heavy chains of a murine, chimeric, veneered or humanized 9E4 antibody so that the cells secrete the antibody into the cell culture media, and purifying the antibody from the cell culture media; and (b) preparing a formulation comprising (i) a chimeric, veneered, or humanized version of antibody 9E4 (ATCC Accession Number PTA-8221), or fragment thereof that specifically competes for binding with 9E4, wherein the antibody is present at a concentration within the range from about 10 mg/mL to about 50 mg/mL; (ii) citrate buffer present at a concentration within the range from about 20 mM to about 30 mM; (iii) trehalose present at a concentration within the range from about 210 mM to about 250 mM; and (iv) polysorbate 20 present at a concentration within the range from about 0.005% to about 0.05% by weight; wherein the formulation is characterized by a pH within the range from about 5.5 to about 6.5. Mammalian cells useful for this purpose include: (a) host cells having stably incorporated into their genomes a nucleic acid sequence encoding a humanized 9E4 light chain set forth as SEQ ID NO: 29 and a humanized 9E4 heavy chain set forth as SEQ ID NO: 31; and (b) host cells having stably incorporated into their genomes a nucleic acid having the nucleotide sequence of SEQ ID NO: 29 and a nucleic acid having the nucleotide sequence of SEQ ID NO: 32. In some aspects of the invention, the disclosed methods of preparing a pharmaceutical formulation include the additional step of evaluating at least one property of the antibody in the formulation, such as physical stability, chemical stability, and/or biological activity.

Further provided are methods of therapeutically or prophylactically treating a human patient having or at risk for a synucleinopathy, the method comprising administering to the patient an effective dosage of a formulation of the invention. Some patients amenable to treatment may have Parkinson's disease.

The disclosed therapeutic and prophylactic treatment methods include combination therapies (i.e., administration of the disclosed antibody formulations with one or more additional drug substances) to thereby elicit synergistic results. The two or more drug substances are administered simultaneously or sequentially, in any order. For example, a formulation of the invention can be administered prior to administration of a second drug substance, concurrently with a second drug substance, or subsequent to administration of a second drug substance. A formulation of the invention can be administered concurrently or consecutively in combination with, e.g., levodopa, benzaseride, carbidopa, dopamine agonists, COMT inhibitors, MAO inhibitors, amantadine, or anticholinergic agents.

In accordance with the disclosed therapeutic and prophylactic treatment methods, formulations of the invention can be administered in multiple dosages, for example, at a frequency in a range of about daily to about annually, such as at a frequency in a range of about every other week to about every three months, or such as once a month or every four weeks. In one aspect, an antibody formulation of the invention is administered intravenously at a dose in a range from about 0.3 mg/kg to about 30 mg/kg drug substance. Exemplary dosage regimes include about 0.3 mg/kg, about 1.0 mg/kg, about 3.0 mg/kg, about 10 mg/kg and about 30 mg/kg of humanized 9E4 drug substance, administered intravenously as a single dose or once every four weeks.

For example, a method of therapeutically or prophylactically treating a human patient having or at risk for a synucleinopathy, such as Parkinson's disease, can comprise administering to the patient an effective dosage of a pharmaceutical formulation comprising: (a) an antibody comprising a light chain having an amino acid sequence comprising SEQ ID NO: 29 and a heavy chain having an amino acid sequence comprising SEQ ID NO: 32, with or without the C-terminal lysine, and which is present at a concentration of about 40 mg/mL; (b) a citrate buffer present at a concentration of about 20 mM; (c) trehalose present at a concentration of about 230 mM; (d) polysorbate 20 present at a concentration of about 0.2 g/L; and (e) a pH of about 6.0. In such a method, the dosage is typically from about 0.3 mg/kg to about 30 mg/kg of the antibody (e.g., about 0.5 mg/kg to about 8 mg/kg, or about 8 mg/kg to about 30 mg/kg) administered intravenously or subcutaneously, at a frequency of from about weekly to about once every 28 days, or about quarterly.

The present invention further provides a pharmaceutical product comprising: (a) a vial comprising about 200 mg antibody in powder form; (b) instructions for reconstitution of the antibody; and (c) instructions for preparing the reconstituted antibody for infusion, wherein for example, (i) the antibody comprises a light chain having an amino acid sequence comprising SEQ ID NO: 29 and a heavy chain having an amino acid sequence comprising SEQ ID NO: 32 with or without the C-terminal lysine; and (ii) the reconstitution instructions require reconstitution with water for injection to an extractable volume of about 5 mL.

BRIEF DESCRIPTION OF THE SEQUENCES

Figure 1:
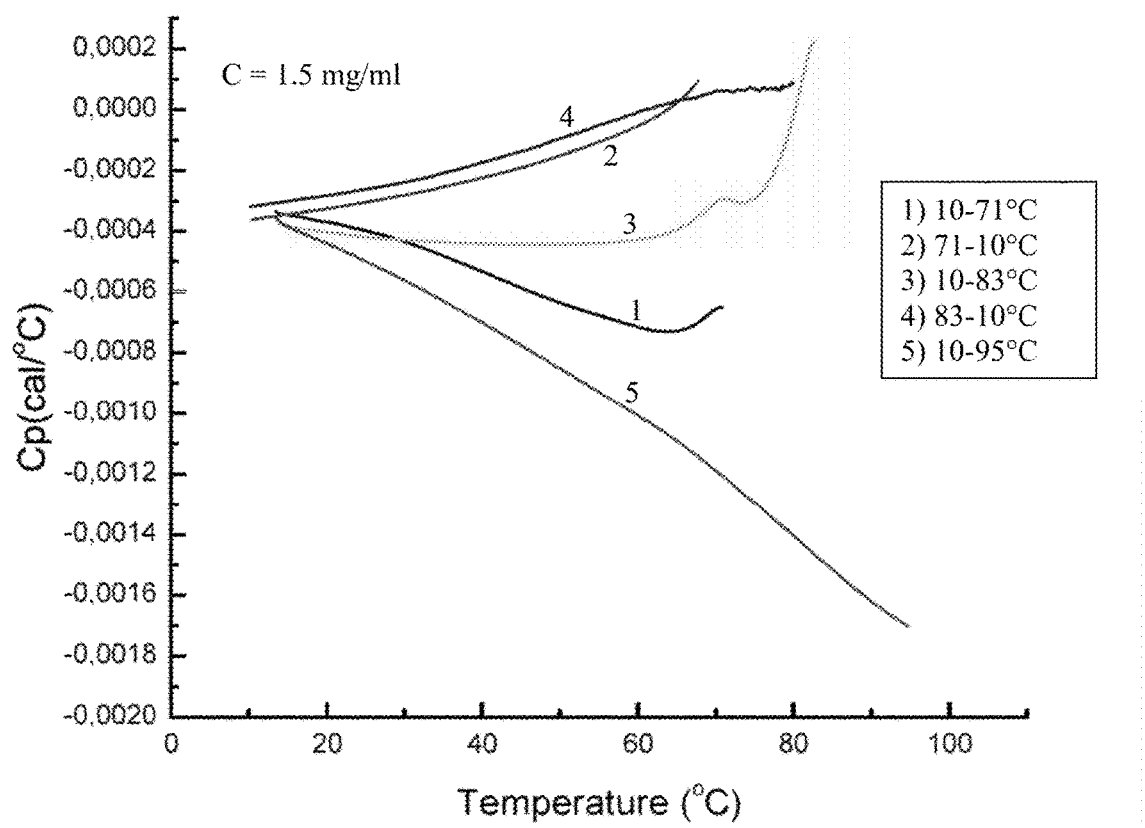
FIG. 1 is a DSC thermogram for humanized 9E4 antibody, showing the energy flow (calories/° C.) associated with increasing or decreasing the temperature of a solution containing 1.5 mg/ml of humanized 9E4 antibody (version H3L3). The antibody solution was heated and cooled sequentially, in the order shown in the inset box. The lines are numbered to indicate which line is associated with each of the five temperature transitions shown in the inset box.

SEQ ID NO:1 is the amino acid sequence of the m9E4VL variable region.

SEQ ID NO:2 is the amino acid sequence of the variable region of the human VL acceptor sequence (NCBI accession code AAY33350).

SEQ ID NO:3 is the amino acid sequence of the Hu9E4VLv1 variable region.

SEQ ID NO:4 is the amino acid sequence of the Hu9E4VLv2 variable region.

SEQ ID NO:5 is the amino acid sequence of the Hu9E4VLv3 variable region.

SEQ ID NO:6 is the amino acid sequence of the m9E4VH variable region.

SEQ ID NO:7 is the amino acid sequence of the variable region of the human VH acceptor sequence (NCBI accession code AAC50998).

SEQ ID NO:8 is the amino acid sequence of the Hu9E4VHv1 variable region.

SEQ ID NO:9 is the amino acid sequence of the Hu9E4VHv2 variable region.

SEQ ID NO:10 is the amino acid sequence of the Hu9E4VHv3 variable region.

SEQ ID NO:11 is the amino acid sequence of the Hu9E4VHv4 variable region.

SEQ ID NO:12 is the amino acid sequence of wild-type human alpha-synuclein.

SEQ ID NO:13 is the amino acid sequence of the humanized 9E4 light chain constant region, with Arginine at the N-terminus.

SEQ ID NO:14 is the amino acid sequence of the humanized 9E4 heavy chain constant region.

SEQ ID NO:15 is the nucleotide sequence encoding the Hu9E4VLv1 variable region.

SEQ ID NO:16 is the nucleotide sequence encoding the Hu9E4VLv2 variable region.

SEQ ID NO:17 is the nucleotide sequence encoding the Hu9E4VLv3 variable region.

SEQ ID NO:18 is the nucleotide sequence encoding the Hu9E4VHv1 variable region.

SEQ ID NO:19 is the nucleotide sequence encoding the Hu9E4VHv2 variable region.

SEQ ID NO:20 is the nucleotide sequence encoding the Hu9E4VHv3 variable region.

SEQ ID NO:21 is the nucleotide sequence encoding the Hu9E4VHv4 variable region.

SEQ ID NO:22 is the amino acid sequence of the Hu9E4VL signal peptide.

SEQ ID NO:23 is the nucleotide sequence encoding the Hu9E4VL signal peptide.

SEQ ID NO:24 is the amino acid sequence of the Hu9E4VH signal peptide.

SEQ ID NO:25 is the nucleotide sequence encoding the Hu9E4VH signal peptide.

SEQ ID NO:26 is the Hu9E4VL consensus amino acid sequence.

SEQ ID NO:27 is the Hu9E4VH consensus amino acid sequence.

SEQ ID NO:28 is the amino acid sequence of the humanized 9E4 light chain constant region, without the Arginine at the N-terminus.

SEQ ID NO:29 is the amino acid sequence of the humanized 9E4 light chain comprising (a) a variable region (version 3), and (b) a constant region with Arginine at the N-terminus.

SEQ ID NO:30 is the amino acid sequence of the humanized 9E4 light chain comprising (a) a variable region (version 3), and (b) a constant region without the Arginine at the N-terminus.

SEQ ID NO:31 is the amino acid sequence of the humanized 9E4 heavy chain comprising (a) a variable region (version 3), and (b) a constant region.

SEQ ID NO:32 is the amino acid sequence of the humanized 9E4 heavy chain comprising (a) a variable region (version 3), and (b) a BIP version heavy chain Glm3 allotype constant region.

SEQ ID NO:33 is the amino acid sequence of the BIP version heavy chain Glm3 allotype constant region.

Definitions

The term "antibody" includes intact antibodies and binding fragments thereof. Typically, fragments compete with the intact antibody from which they were derived for specific binding to the target. Fragments include separate heavy chains, separate light chains, Fab, Fab', F(ab')2, F(ab)c, Fv, single chain antibodies, and single domain antibodies. The term "antibody" also includes a bispecific antibody. A bispecific or bifunctional antibody is an artificial hybrid antibody having two different heavy/light chain pairs and two different binding sites (see, e.g., Songsivilai and Lachmann, Clin. Exp. Immunol., 79:315-321 (1990); Kostelny et al., J. Immunol., 148:1547-53 (1992)).

The basic antibody structural unit is a tetramer of subunits. Each tetramer includes two identical pairs of polypeptide chains, each pair having one "light" chain (about 25 kDa) and one "heavy" chain (about 50-70 kDa). The amino-terminal portion of each chain includes a variable region of about 100 to 110 or more amino acids primarily responsible for antigen recognition. When initially expressed, this variable region is typically linked to a cleavable signal peptide. The variable region without the signal peptide is sometimes referred to as a mature variable region. Thus, for example, a light chain mature variable region means a light chain variable region without the light chain signal peptide. The carboxy-terminal portion of each chain defines a constant region primarily responsible for effector function. A constant region can include any or all of a CH1 region, hinge region, CH2 region, and CH3 region.

Light chains are classified as either kappa or lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acids, with the heavy chain also including a "D" region of about 10 or more amino acids. (See generally, Fundamental Immunology (Paul, W., ed., 2nd ed. Raven Press, N.Y., 1989), Ch. 7) (incorporated by reference in its entirety for all purposes).

The mature variable regions of each light/heavy chain pair form the antibody binding site. Thus, an intact antibody has two binding sites. Except for bifunctional or bispecific antibodies, the two binding sites are the same. The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the regions FR1, CDR1, FR2, CDR2, FR3, CDR3 and FR4. The assignment of amino acids to each region is in accordance with the definitions of Kabat, Sequences of Proteins of Immunological Interest (National Institutes of Health, Bethesda, Md., 1987 and 1991), or Chothia & Lesk, J. Mol. Biol. 196:901-917 (1987); Chothia et al., Nature 342:878-883 (1989). Kabat also provides a widely used numbering convention (Kabat numbering) in which corresponding residues between different heavy chains or between different light chains are assigned the same number.

Percentage sequence identities are determined with antibody sequences maximally aligned by the Kabat numbering convention. After alignment, if a subject antibody region (e.g., the entire mature variable region of a heavy or light chain) is being compared with the same region of a reference antibody, the percentage sequence identity between the subject and reference antibody regions is the number of positions occupied by the same amino acid in both the subject and reference antibody region divided by the total number of aligned positions of the two regions (with gaps not counted) multiplied by 100 to convert to percentage.

For purposes of classifying amino acids substitutions as conservative or non-conservative, amino acids are grouped as follows: Group I (hydrophobic sidechains): Norleucine, Met, Ala, Val, Leu, Ile; Group II (neutral hydrophilic side chains): Cys, Ser, Thr; Group III (acidic side chains): Asp, Glu; Group IV (basic side chains): Asn, Gln, His, Lys, Arg; Group V (residues influencing chain orientation): Gly, Pro; and Group VI (aromatic side chains): Trp, Tyr, Phe. Conservative substitutions involve substitutions between amino acids in the same class.

Non-conservative substitutions constitute exchanging a member of one of these classes for a member of another.

Antibodies of the invention typically bind to their designated target with an affinity constant of at least $10^6$, $10^7$, $10^8$, $10^9$, or $10^{10}$ $M^{-1}$. Such binding is specific binding in that it is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces. Specific binding does not, however, necessarily imply that a monoclonal antibody binds one and only one target.

The term "symptom" refers to subjective evidence of a disease, such as altered gait, as perceived by a subject. A "sign" refers to objective evidence of a disease as observed by a physician.

An individual is at increased risk of a disease if the subject has at least one known risk-factor (e.g., genetic, biochemical, family history, situational exposure) placing individuals with that risk factor at a statistically significant greater risk of developing the disease than individuals without the risk factor. Statistical significance means p≤0.05.

Unless otherwise apparent from the context, the term "about" encompasses values within the standard deviation of the mean of a stated value or +/−5% of a stated value, whichever is greater.

The term "9E4 antibody" refers to any antibody in which each of the CDRs is substantially that of 9E4, and thus includes murine, chimeric, veneered, and humanized 9E4.

Unless otherwise apparent from the context, reference to a range includes any integer within the range.

DETAILED DESCRIPTION

I. General

9E4 is an antibody binding to an epitope within amino acid residues 118-126 of human alpha-synuclein. Humanized forms of the antibody are described in WO/2013/063516, incorporated by reference in its entirety for all purposes. The present application provides liquid and lyophilized formulations incorporating chimeric, veneered, or humanized forms of 9E4 (sometimes referred to as 9E4 antibodies). The formulations are designed to have combinations of components conferring stability on the antibody as further described below.

II. Target Molecules

Natural human wildtype alpha-synuclein is a peptide of 140 amino acids having the following amino acid sequence:

```
                                           (SEQ ID NO: 12)
MDVFMKGLSK AKEGVVAAAE KTKQGVAEAA GKTKEGVLYV

GSKTKEGVVH GVATVAEKTK EQVTNVGGAV VTGVTAVAQK

TVEGAGSIAA ATGFVKKDQL GKNEEGAPQE GILEDMPVDP

DNEAYEMPSE EGYQDYEPEA
```

(Ueda et al., Proc. Natl. Acad. Sci. USA (1993) 90:11282-6); GenBank accession number: P37840. The protein has three recognized domains: a KTKE repeat domain covering amino acids 1-61; a NAC (Non-amyloid component) domain running from about amino acids 60-95; and a C-terminal acidic domain running from about amino acid 98 to 140.

Unless otherwise apparent from the context, reference to alpha-synuclein or its fragments includes the natural human wildtype amino acid sequences indicated above, and human allelic variants thereof, particularly those associated with Lewy body disease (e.g., variants E46K, A30P and A53T, with the first letter indicating the amino acid in SEQ ID NO:12, the number indicating the codon position in SEQ ID NO:12, and the second letter indicating the amino acid in the allelic variant). Such variants can optionally be present individually or in any combination in any of the aspects of the invention described below. The induced mutations E83Q, A90V, A76T, which enhance alpha synuclein aggregation, can also be present individually or in combination with each other and/or human allelic variants E46K, A30P and A53T.

III. Lewy Body Diseases

Lewy Body Diseases (LBD) are characterized by degeneration of the dopaminergic system, motor alterations, cognitive impairment, and formation of Lewy bodies (LBs). (McKeith et al., Neurology (1996) 47:1113-24). Lewy Bodies are spherical protein deposits found in nerve cells. Their presence in the brain disrupts the brain's normal function interrupting the action of chemical messengers including acetylcholine and dopamine. Lewy Body diseases include Parkinson's disease (including idiopathic Parkinson's disease), Diffuse Lewy Body Disease (DLBD), also known as Dementia with Lewy Bodies (DLB), Lewy Body variant of Alzheimer's disease (LBV), Combined Alzheimer's and Parkinson disease, and multiple system atrophy (MSA; e.g., Olivopontocerebellar Atrophy, Striatonigral Degeneration, and Shy-Drager Syndrome). DLBD shares symptoms of both Alzheimer's and Parkinson's disease. DLBD differs from Parkinson's disease mainly in the location of Lewy Bodies. In DLBD, Lewy Bodies form mainly in the cortex. In Parkinson's disease, they form mainly in the substantia nigra. Other Lewy Body diseases include Pure Autonomic Failure, Lewy Body dysphagia, Incidental LBD, and Inherited LBD (e.g., mutations of the alpha-synuclein gene, PARK3 and PARK4).

IV. Humanized 9E4 Antibodies

A. Binding Specificity and Functional Properties

Humanized antibodies of the invention specifically bind to human alpha synuclein. The affinity of some humanized antibodies (i.e., Ka) is preferably within a factor of five or two of that of the mouse antibody 9E4. Some humanized antibodies have an affinity that is the same (within experimental error) or greater than that of the mouse 9E4 antibody. Preferred humanized antibodies bind to the same epitope and/or compete with the mouse antibody 9E4 for binding to human alpha synuclein.

In some antibodies, humanized 9E4 forms one arm of a bispecific antibody, the other arm of which is an antibody that binds to a receptor expressed on the blood brain barrier, such as an insulin receptor, an insulin-like growth factor (IGF) receptor, a leptin receptor, or a lipoprotein receptor, or preferably a transferrin receptor (Friden et al., PNAS 88:4771-4775, 1991; Friden et al., Science 259:373-377, 1993). Such a bispecific antibody can be transferred cross the blood brain barrier by receptor-mediated transcytosis. Brain uptake of the bispecific antibody can be further enhanced by engineering the bi-specific antibody to reduce its affinity to the blood brain barrier receptor. Reduced affinity for the receptor resulted in a broader distribution in the brain (see, e.g., Atwal. et al. Sci. Trans. Med. 3, 84ra43, 2011; Yu et al. Sci. Trans. Med. 3, 84ra44, 2011).

Exemplary bispecific antibodies can also be (1) a dual-variable-domain antibody (DVD-Ig), where each light chain and heavy chain contains two variable domains in tandem through a short peptide linkage (Wu et al., Generation and Characterization of a Dual Variable Domain Immunoglobulin (DVD-Ig™) Molecule, In: Antibody Engineering, Springer Berlin Heidelberg (2010)); (2) a Tandab, which is a fusion of two single chain diabodies resulting in a tetravalent bispecific antibody that has two binding sites for each of the target antigens; (3) a flexibody, which is a combination of scFvs with a diabody resulting in a multivalent molecule; (4) a so called "dock and lock" molecule, based on the "dimerization and docking domain" in Protein Kinase A, which, when applied to Fabs, can yield a trivalent bispecific binding protein consisting of two identical Fab fragments linked to a different Fab fragment; (5) a so-called Scorpion molecule, comprising, e.g., two scFvs fused to both termini of a human Fc-region. Examples of platforms useful for preparing bispecific antibodies include but are not limited to BiTE (Micromet), DART (MacroGenics), Fcab and Mab2 (F-star), Fc-engineered IgG1 (Xencor) or DuoBody (based on Fab arm exchange, Genmab).

B. Humanized Antibodies

A humanized antibody is a genetically engineered antibody in which the CDRs from a non-human "donor" antibody are grafted into human "acceptor" antibody sequences (see, e.g., Queen et al., U.S. Pat. Nos. 5,530,101 and 5,585,089; Winter et al., U.S. Pat. No. 5,225,539, Carter, U.S. Pat. No. 6,407,213, Adair, U.S. Pat. Nos. 5,859,205 6,881,557, Foote, U.S. Pat. No. 6,881,557). The acceptor antibody sequences can be, for example, a mature human antibody variable region sequence, a composite of such sequences, a consensus sequence of human antibody sequences (e.g., light and heavy chain variable region consensus sequences of Kabat, 1991, supra), or a germline variable region sequence. A preferred acceptor sequence for the heavy chain is the human mature heavy chain variable region of NCBI accession code AAC50998 (GI: 1791009) or other mature heavy chain variable region derived from germline IGHV3-7'01 or IGHV3-7'02 (clone name V3-7 or VH3-11) (Glas et al., Clin Exp Immunol. 107:372-80, 1997), or a mature heavy chain variable region sequence incorporating one of these germ line sequences. For the light chain, a preferred acceptor sequence is the light chain mature variable region with NCBI accession code AAY33350 (GI: 63102889) or other mature light chain sequence derived from the germline IGKV1D-39 or IGKV1-39 (clone name O2 or O12) (Kramer et al., Eur J Immunol. 35:2131-45, 2005), or a light chain mature variable region sequence incorporating one of these germ line sequences. Thus, a humanized antibody of the invention includes antibodies having three light chain and three heavy chain CDRs as defined by Kabat from the murine 9E4 antibody (donor antibody) and mature variable region framework sequences and constant regions, if present, entirely or substantially from human antibody sequences. Likewise a humanized heavy chain includes heavy chains having three heavy chain CDRs as defined by Kabat from the heavy chain of the murine 9E4 antibody, and a mature heavy chain variable sequence and heavy chain constant region sequence, if present, entirely or substantially from human antibody heavy chain sequences. Likewise a humanized light chain includes light chains having three light chain CDRs as defined by Kabat from the light chain of the murine 9E4 antibody, and a mature light chain variable sequence and light chain constant region sequence, if present, entirely or substantially from human antibody light chain sequences. The mature variable region framework sequences of an antibody chain or the constant region sequence of an antibody chain are substantially from a human mature variable region framework sequence or human constant region sequence, respectively, when at least 85%, 90%, 95%, 96%, 97%, 98%, 99% or 100% of corresponding residues defined by Kabat are identical.

Certain amino acids from the human mature variable region framework residues can be selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

For example, when an amino acid differs between a murine mature variable region framework residue and a selected human mature variable region framework residue, the human framework amino acid can be substituted by the equivalent framework amino acid from the mouse antibody when it is reasonably expected that the amino acid:

(1) noncovalently binds antigen directly,
(2) is adjacent to a CDR region,
(3) otherwise interacts with a CDR region (e.g. is within about 6 Å of a CDR region)
(4) mediates interaction between the heavy and light chains.

The invention provides formulations including humanized forms of the mouse 9E4 antibody including three exemplified humanized light chain mature variable regions (Hu9E4VLv1-v3; SEQ ID NOs:3-5) and four exemplified humanized heavy chain mature variable regions (Hu9E4VHv1-v4; SEQ ID NOs:8-11). SEQ ID NO:4 includes the three Kabat CDRs of the mouse 9E4 light chain and the mature variable region frameworks of AAY33350. SEQ ID NOS. 3 and 5 include backmutations as shown in Table 2. SEQ ID NO: 11 includes the three Kabat CDRs of mouse 9E4 and the mature variable region frameworks of AAC50998. SEQ ID NOs:8-10 include backmutations as shown in Table 3.

The invention provides formulations including variants of a humanized 9E4 antibody disclosed herein, in which the humanized heavy chain mature variable region shows at least 90%, 95% or 99% identity to SEQ ID NOs:8-11 and the humanized light chain mature variable region shows at least 90, 95 or 99% sequence identity to SEQ ID NOs:3-5, but in which any variation from the designated SEQ ID NO: occurs in a mature variable region framework rather than a Kabat CDR. In some such antibodies, position L36 is occupied by Y or F, and/or position L83 is occupied by F or L, and/or position H73 is occupied by N or D and/or position H93 is occupied by A or S (all positions here, as elsewhere, in this application are by Kabat numbering). In some such antibodies, some or all of the backmutations in Hu9E4VLv1-v3 and Hu9E4VHv1-v4 are retained. In other words, one or both of heavy chain positions H73 and H93 is occupied by D and A, respectively. Likewise, in some antibodies, one or both of light chain positions L36 and L83 is occupied by F and L, respectively. In some antibodies, 1, 2, 3 or all four of positions H73, H93, L36 and L83 is/are occupied by D, A, F and L, respectively. In some antibodies, 0, 1, or 2 positions are changed in the heavy chain mature variable region framework relative to SEQ ID NO:11, and 0, 1, or 2 positions are change in the light chain mature variable region framework relative to SEQ ID NO:4.

The invention provides formulations in which some antibodies comprise a humanized heavy chain comprising the three Kabat CDRs of SEQ ID NO:11 and a humanized light chain comprising the three Kabat CDRs of SEQ ID NO:4, provided that position L36 (Kabat numbering) is occupied by F or Y and/or position L83 (Kabat numbering) is occupied by L or F and/or position H73 (Kabat numbering) is occupied by D or N, and/or position H93 (Kabat numbering) is occupied by S or A. In some such antibodies, position L36 (Kabat numbering) is occupied by F. In some such antibodies, position L36 (Kabat numbering) is occupied by F and position L83 (Kabat numbering) is occupied by L. In some such antibodies, position L36 (Kabat numbering) is occupied by F and position H73 (Kabat numbering) is occupied by D. In some such antibodies, position L36 (Kabat numbering) is occupied by F and position H93 (Kabat numbering) is occupied by S. In some such antibodies, position L36 (Kabat numbering) is occupied by F and position H93 (Kabat numbering) is occupied by A. In some such antibodies, position L36 (Kabat numbering) is occupied by F, position L83 (Kabat numbering) is occupied by L, and position H73 (Kabat numbering) is occupied by D. In some such antibodies, position L36 (Kabat numbering) is occupied by F, position L83 (Kabat numbering) is occupied by L, and position H93 (Kabat numbering) is occupied by S. In some such antibodies, position L36 (Kabat numbering) is occupied by F, position L83 (Kabat numbering) is occupied by L, and position H93 (Kabat numbering) is occupied by A. In some such antibodies, position L36 (Kabat numbering) is occupied by F, position H73 (Kabat numbering) is occupied by D, and position H93 (Kabat numbering) is occupied by S. In some such antibodies, position L36 (Kabat numbering) is occupied by F, position L83 is occupied by F, position H73 (Kabat numbering) is occupied by D, and position H93 (Kabat numbering) is occupied by S. In some such antibodies, position L36 (Kabat numbering) is occupied by F, position H73 (Kabat numbering) is occupied by D, and position H93 (Kabat numbering) is occupied by A. In some such antibodies, position L36 (Kabat numbering) is occupied by F, position L83 (Kabat numbering) is occupied by L, position H73 (Kabat numbering) is occupied by D, and position H93 (Kabat numbering) is occupied by S. In some such antibodies, position L36 (Kabat numbering) is occupied by F, position L83 (Kabat numbering) is occupied by L, position H73 (Kabat numbering) is occupied by D, and position H93 (Kabat numbering) is occupied by A. In some such antibodies, position L83 (Kabat numbering) is occupied by L. In some such antibodies, position L83 (Kabat numbering) is occupied by L and position H73 (Kabat numbering) is occupied by D. In some such antibodies, position L83 (Kabat numbering) is occupied by L and position H93 (Kabat numbering) is occupied by S. In some such antibodies, position L83 (Kabat numbering) is occupied by L and position H93 (Kabat numbering) is occupied by A. In some such antibodies, position L83 (Kabat numbering) is occupied by L, position H73 (Kabat numbering) is occupied by D, and position H93 (Kabat numbering) is occupied by S. In some such antibodies, position L83 (Kabat numbering) is occupied by L, position H73 (Kabat numbering) is occupied by D, and position H93 (Kabat numbering) is occupied by A. In some such antibodies, position H73 (Kabat numbering) is occupied by D. In some such antibodies, position H73 (Kabat numbering) is occupied by D and position H93 (Kabat numbering) is occupied by S. In some such antibodies, position H73 (Kabat numbering) is occupied by D and position H93 (Kabat numbering) is occupied by A. In some such antibodies, position H93 (Kabat numbering) is occupied by S. In some such antibodies, position H93 (Kabat numbering) is occupied by A. In some such antibodies, position L36 is occupied by Y, position L83 is occupied by F, position H73 is occupied by N and position H93 is occupied by S. Some exemplary antibodies with desirable residues at positions L36, L83, H73, and H93 and combinations thereof are listed in Table 1 below.

TABLE 1

Exemplary antibodies with desirable residues at positions L36, L83, H73, and H93 (Kabat numbering).

| Exemplary Antibody | L36 | L83 | H73 | H93 |
|---|---|---|---|---|
| 1 | F | F | N | A |
| 2 | F | L | N | A |
| 3 | F | F | D | A |
| 4 | F | F | N | S |
| 5 (version 3) | F | L | D | A |

TABLE 1-continued

Exemplary antibodies with desirable residues at positions L36, L83, H73, and H93 (Kabat numbering).

| Exemplary Antibody | L36 | L83 | H73 | H93 |
|---|---|---|---|---|
| 6 | F | L | N | S |
| 7 (version 1) | F | F | D | S |
| 8 | F | L | D | S |
| 9 | Y | L | N | A |
| 10 | Y | L | D | A |
| 11 | Y | L | N | S |
| 12 | Y | L | D | S |
| 13 | Y | F | D | A |
| 14 | Y | F | D | S |
| 15 (version 2) | Y | F | N | S |

TABLE 2

$V_H$ Backmutations

| $V_H$ variant | $V_H$ exon acceptor sequence | donor framework residues |
|---|---|---|
| Hu9E4VHv1 | NCBI accession code AAC50998 | H73, H93 |
| Hu9E4VHv2 | NCBI accession code AAC50998 | H93 |
| Hu9E4VHv3 | NCBI accession code AAC50998 | H73 |

TABLE 3

$V_L$ Backmutations

| $V_L$ variant | $V_L$ exon acceptor sequence | donor framework residues |
|---|---|---|
| Hu9E4VLv1 | NCBI accession code AAY33350 | L36 |
| Hu9E4VLv2 | NCBI accession code AAY33350 | None |
| Hu9E4VLv3 | NCBI accession code AAY33350 | L36, L83 |

In some antibodies, the heavy chain mature variable region has an amino acid sequence designated SEQ ID NO:10. In some antibodies, the light chain mature variable region has an amino acid sequence designated SEQ ID NO:5 or SEQ ID NO:3. In some such antibodies, the heavy chain mature variable region has an amino acid sequence designated SEQ ID NO:10, and the light chain mature variable region has an amino acid sequence designated SEQ ID NO:5 or SEQ ID NO:3. In some such antibodies, the heavy chain mature variable region has an amino acid sequence designated SEQ ID NO:10, and the light chain mature variable region has an amino acid sequence designated SEQ ID NO:5.

Other amino acid substitutions can be made in the mature variable region framework, for example, in residues not in contact with the CDRs. Often the replacements made in the variant humanized sequences are conservative with respect to the replaced amino acids. In some antibodies, replacements relative to Hu9E4VLv1-v3 and Hu9E4VHv1-v4 (whether or not conservative) have no substantial effect on the binding affinity or potency of the resultant antibody relative to Hu9E4VLv1-v3 and Hu9E4VHv1-v4, that is, its ability to bind human alpha synuclein.

Variants typically differ from the heavy and light chain mature variable region sequences of Hu9E4VLv1-v3 and Hu9E4VHv1-v4 by a small number (e.g., typically no more than 1, 2, 3, 5 or 10 in either the light chain or heavy chain mature variable region framework, or both) of replacements, deletions or insertions.

The formulations described below can include any of the humanized 9E4 chains described above, or in the sequence listing or elsewhere in the application in any combination of light and heavy chains forming a humanized 9E4 antibody specifically binding to human alpha-synuclein.

C. Chimeric and Veneered Antibodies

The invention further provides chimeric and veneered forms of non-human antibodies, particularly 9E4.

A chimeric antibody is an antibody in which the mature variable regions of light and heavy chains of a non-human antibody (e.g., a mouse) are combined with light and heavy chain constant regions from an antibody of a different species. Typically, the light and heavy chain constant regions are of human origin, but the constant regions can originate from a different non-human species, such as a rat, as needed (e.g., to facilitate testing of the non-human antibody in an appropriate animal model). Such antibodies substantially or entirely retain the binding specificity of the non-human (e.g., mouse) antibody supplying the variable regions, and are about two-thirds human (or different non-human species) sequence.

A veneered antibody is a type of humanized antibody that retains some and usually all of the CDRs and some of the non-human variable region framework residues of a non-human antibody but replaces other variable region framework residues that may contribute to B- or T-cell epitopes, for example exposed residues (Padlan, Mol. Immunol. 28:489, 1991) with residues from the corresponding positions of a human antibody sequence. The result is an antibody in which the CDRs are entirely or substantially from a non-human antibody and the variable region frameworks of the non-human antibody are made more human-like by the substitutions. Veneered forms of 9E4 are included in the invention.

D. Selection of Constant Region

The heavy and light chain variable regions of chimeric, veneered or humanized antibodies can be linked to at least a portion of a human constant region. The choice of constant region depends, in part, whether antibody-dependent cell-mediated cytotoxicity, antibody dependent cellular phagocytosis and/or complement dependent cytotoxicity are desired. For example, human isotopes IgG1 and IgG3 have complement-dependent cytotoxicity and human isotypes IgG2 and IgG4 do not. Human IgG1 and IgG3 also induce stronger cell mediated effector functions than human IgG2 and IgG4. Light chain constant regions can be lambda or kappa. An exemplary human light chain kappa constant region has the amino acid sequence of SEQ ID NO:13. Some such light chain kappa constant regions can be encoded by a nucleic acid sequence. The N-terminal arginine of SEQ ID NO:13 can be omitted, in which case light chain kappa constant region has the amino acid sequence of SEQ ID NO:28. Some such light chain kappa constant regions can be encoded by a nucleic acid sequence. An exemplary human IgG1 heavy chain constant region has the amino acid sequence of SEQ ID NO:14 (with or without the C-terminal lysine) or the heavy chain constant region component of SEQ ID NO:31. Some such heavy chain constant regions can be encoded by a nucleic acid sequence. Antibodies can be expressed as tetramers containing two light and two heavy chains, as separate heavy chains, light chains, as Fab, Fab', F(ab')2, and Fv, or as single chain antibodies in which heavy and light chain mature variable domains are linked through a spacer.

Human constant regions show allotypic variation and isoallotypic variation between different individuals, that is, the constant regions can differ in different individuals at one or more polymorphic positions. Isoallotypes differ from allotypes in that sera recognizing an isoallotype bind to a non-polymorphic region of a one or more other isotypes. Thus, for example, another heavy chain constant region is of IgG1 G1m3 allotype and has the amino acid sequence encoding a constant region of SEQ ID NO:32. Another heavy chain constant region has the amino acid sequence of SEQ ID NO:33. Yet another heavy chain constant region has the amino acid sequence encoding a content region of SEQ ID NO:32 except that it lacks the C-terminal lysine. Yet another heavy chain constant region has the amino acid sequence of SEQ ID NO:33 except that it lacks the C-terminal lysine.

One or several amino acids at the amino or carboxy terminus of the light and/or heavy chain, such as the C-terminal lysine of the heavy chain, may be missing or derivatized in a proportion or all of the molecules. Substitutions can be made in the constant regions to reduce or increase effector function such as complement-mediated cytotoxicity or ADCC (see, e.g., Winter et al., U.S. Pat. No. 5,624,821; Tso et al., U.S. Pat. No. 5,834,597; and Lazar et al., Proc. Natl. Acad. Sci. USA 103:4005, 2006), or to prolong half-life in humans (see, e.g., Hinton et al., J. Biol. Chem. 279:6213, 2004). Exemplary substitutions include a Gln at position 250 and/or a Leu at position 428 (EU numbering is used in this paragraph for the constant region) for increasing the half-life of an antibody. Substitution at any or all of positions 234, 235, 236 and/or 237 reduce affinity for Fcγ receptors, particularly FcγRI receptor (see, e.g., U.S. Pat. No. 6,624,821). Some antibodies have alanine substitution at positions 234, 235 and 237 of human IgG1 for reducing effector functions. Optionally, positions 234, 236 and/or 237 in human IgG2 are substituted with alanine and position 235 with glutamine (see, e.g., U.S. Pat. No. 5,624,821).

E. Expression of Recombinant Antibodies

Antibodies can be produced by recombinant expression. Nucleic acids encoding the antibodies can be codon-optimized for expression in the desired cell-type (e.g., CHO or Sp2/0). Recombinant nucleic acid constructs typically include an expression control sequence operably linked to the coding sequences of antibody chains, including naturally-associated or heterologous promoter regions. The expression control sequences can be eukaryotic promoter systems in vectors capable of transforming or transfecting eukaryotic host cells. Once the vector has been incorporated into the appropriate host, the host is maintained under conditions suitable for high level expression of the nucleotide sequences, and the collection and purification of the crossreacting antibodies. The vector or vectors encoding the antibody chains can also contain a selectable gene, such as dihydrofolate reductase, to allow amplification of copy number of the nucleic acids encoding the antibody chains.

*E. coli* is a prokaryotic host particularly useful for expressing antibodies, particularly antibody fragments. Microbes, such as yeast are also useful for expression. *Saccharomyces* is a preferred yeast host, with suitable vectors having expression control sequences, an origin of replication, termination sequences and the like as desired. Typical promoters include 3-phosphoglycerate kinase and other glycolytic enzymes. Inducible yeast promoters include, among others, promoters from alcohol dehydrogenase, isocytochrome C, and enzymes responsible for maltose and galactose utilizations.

Mammalian cells can be used for expressing nucleotide segments encoding immunoglobulins or fragments thereof. See Winnacker, From Genes to Clones, (VCH Publishers, NY, 1987). A number of suitable host cell lines capable of secreting intact heterologous proteins have been developed in the art, and include CHO cell lines, various COS cell lines, HeLa cells, HEK293 cells, L cells, and non-antibody-producing myelomas including Sp2/0 and NS0. It can be advantageous to use nonhuman cells. Expression vectors for these cells can include expression control sequences, such as an origin of replication, a promoter, an enhancer (Queen et al., *Immunol. Rev.* 89:49 (1986)), and necessary processing information sites, such as ribosome binding sites, RNA splice sites, polyadenylation sites, and transcriptional terminator sequences. Suitable expression control sequences are promoters derived from endogenous genes, cytomegalovirus, SV40, adenovirus, bovine papillomavirus, and the like. See Co et al., *J. Immunol.* 148:1149 (1992).

Having introduced vector(s) encoding antibody heavy and light chains into cell culture, cell pools can be screened for growth productivity and product quality in serum-free media. Top-producing cell pools can then be subjected of FACS-based single-cell cloning to generate monoclonal lines. Specific productivities above 50 pg or 100 pg per cell per day, which correspond to product titers of greater than 7.5 g/L culture, can be advantageous. Antibodies produced by single cell clones can also be tested for turbidity, filtration properties, PAGE, IEF, UV scan, HP-SEC, carboydrate-oligosaccharide mapping, mass spectrometery, and bining assay, such as ELISA or Biacore. A selected clone can then be banked in multiple vials and stored frozen for subsequent use.

Once expressed, antibodies can be purified according to standard procedures of the art, including protein A capture, column chromatography (e.g., hydrophobic interaction or ion exchange), low-pH for viral inactivation and the like (see generally, Scopes, Protein Purification (Springer-Verlag, NY, 1982)).

Methodology for commercial production of antibodies including codon optimization, selection of promoters, transcription elements, and terminators, serum-free single cell cloning, cell banking, use of selection markers for amplification of copy number, CHO terminator, serum free single cell cloning, improvement of protein titers (see, e.g., U.S. Pat. Nos. 5,786,464, 6,114,148, 6,063,598, 7,569,339, WO2004/050884, WO2008/012142, WO2008/012142, WO2005/019442, WO2008/107388, and WO2009/027471, and U.S. Pat. No. 5,888,809).

V. Nucleic Acids

The invention further provides nucleic acids encoding any of the heavy and light chains described above. Typically, the nucleic acids also encode a signal peptide fused to the mature heavy and light chains (e.g., signal peptides having amino acid sequences of SEQ ID NOS: 22 and 24 that can be encoded by SEQ ID NOS: 23 and 25). Coding sequences on nucleic acids can be in operable linkage with regulatory sequences to ensure expression of the coding sequences, such as a promoter, enhancer, ribosome binding site, transcription termination signal and the like. The nucleic acids encoding heavy and light chains can occur in isolated form or can be cloned into one or more vectors. The nucleic acids can be synthesized by for example, solid state synthesis or PCR of overlapping oligonucleotides. Nucleic acids encoding heavy and light chains can be joined as one contiguous nucleic acid, e.g., within an expression vector, or can be separate, e.g., each cloned into its own expression vector.

VI. Therapeutic Applications

The invention provides several methods of treating or effecting prophylaxis of Lewy Body disease in patients suffering from or at risk of such disease. Patients amenable to treatment include individuals at risk of disease of a LBD but not showing symptoms, as well as patients presently showing symptoms or the early warning signs of synucleinopathies, for example, EEG slowing, neuropsychiatric manifestations (depression, dementia, hallucinations, anxiety, apathy, anhedonia), autonomic changes (orthostatic hypotension, bladder disturbances, constipation, fecal incontinence, sialorrhea, dysphagia, sexual dysfunction, changes in cerebral blood flow), sensory changes (olfactory, pain, color discrimination abnormal sensations), sleep disorders (REM sleep behavior disorder (RBD), restless legs syndrome/periodic extremity movements, hypersomnia, insomnia) and miscellaneous other signs and symptoms (fatigue, diplopia, blurred vision, seborrhea, weight loss/gain). Therefore, the present methods can be administered prophylactically to individuals who have a known genetic risk of a LBD. Such individuals include those having relatives who have experienced this disease, and those whose risk is determined by analysis of genetic or biochemical markers. Genetic markers of risk toward PD include mutations in the alpha-synuclein or Parkin, UCHLI, and CYP2D6 genes; particularly mutations at positions 30 and 53 of the alpha-synuclein gene. Individuals presently suffering from Parkinson's disease can be recognized from its clinical manifestations including resting tremor, muscular rigidity, bradykinesia and postural instability.

In asymptomatic patients, treatment can begin at any age (e.g., 10, 20, 30). Usually, however, it is not necessary to begin treatment until a patient reaches 40, 50, 60 or 70. Treatment typically entails multiple dosages over a period of time. Treatment can be monitored by assaying antibody, or activated T-cell or B-cell responses to a therapeutic agent (e.g., a truncated form of alpha-synuclein peptide) over time. If the response falls, a booster dosage is indicated.

Antibodies can be used for treating or effecting prophylaxis of Lewy Body disease in patients by administration under conditions that generate a beneficial therapeutic response in a patient (e.g., reduction of neuritic and/or axonal alpha synuclein aggregates, reduction of neuritic dystrophy, improving cognitive function, and/or reversing, treating or preventing cognitive decline) in the patient. In some methods, the areas of neuritic dystrophy in the neuropil of neocortex and/or basal ganglia can be reduced by on average at least 10%, 20%, 30%, or 40% in treated patients compared with a control population.

Cognitive impairment, progressive decline in cognitive function, changes in brain morphology, and changes in cerebrovascular function are commonly observed in patients suffering from or at risk of Lewy Body disease. Administration of the present antibodies can inhibit or delay decline of cognitive function in such patients.

The invention also provides methods of preserving or increasing synaptic density and/or dentritic density. An index of changes in synaptic or dentritic density can be measured by markers of synapse formation (synaptophysin) and/or dendrites (MAP2). In some methods, the synaptic or dentritic density can be restored to the level of synaptic or dentritic density in a healthy subject. In some methods, the mean level of synaptic or dentritic density in treated patients can be elevated by 5%, 10%, 15%, 20%, 25%, 30% or more as compared to a population of untreated control patients.

VII. Methods of Treatment

In prophylactic applications, an antibody or agent for inducing an antibody or a formulation including the same is administered to a patient susceptible to, or otherwise at risk of a disease in a regime (dose, frequency and route of administration) effective to reduce the risk, lessen the severity, or delay the onset of at least one sign or symptom of the disease. In some prophylactic applications, the regime is effective to inhibit or delay accumulation of alpha synuclein and truncated fragments in the brain, and/or inhibit or delay its toxic effects and/or inhibit/or delay development of behavioral deficits. In therapeutic applications, an antibody or agent to induce an antibody is administered to a patient suspected of, or already suffering from a Lewy body disease in a regime (dose, frequency and route of administration) effective to ameliorate or at least inhibit further deterioration of at least one sign or symptom of the disease. In some therapeutic applications, the regime is effective to reduce or at least inhibit further increase of levels of alpha synuclein and truncated fragments, associated toxicities and/or behavioral deficits.

A regime is considered therapeutically or prophylactically effective if an individual treated patient achieves an outcome more favorable than the mean outcome in a control population of comparable patients not treated by methods of the invention, or if a more favorable outcome is demonstrated in treated patients versus control patients in a controlled clinical trial (e.g., a phase II, phase II/III or phase III trial) at the $p<0.05$ or 0.01 or even 0.001 level.

Effective doses vary depending on many different factors, including means of administration, target site, physiological state of the patient including type of Lewy body disease, whether the patient is an ApoE carrier, whether the patient is human or an animal, other medications administered, and whether treatment is prophylactic or therapeutic.

An exemplary dosage range for antibodies is from about 0.1 to 50 mg/kg of patient body weight. Antibody can be administered such doses daily, on alternative days, weekly, fortnightly, monthly, quarterly, annually or according to any other schedule determined by empirical analysis. An exemplary treatment entails administration in multiple dosages over a prolonged period, for example, of at least six months. Additional exemplary treatment regimes entail administration once per every two weeks or once a month or once every 3 to 6 months.

Antibodies can be administered via a peripheral route (i.e., one in which an administered antibody crosses the blood brain barrier to reach an intended site in the brain. Routes of administration include topical, intravenous, oral, subcutaneous, intraarterial, intracranial, intrathecal, intraperitoneal, intranasal or intramuscular. Some routes for administration of antibodies are intravenous and subcutaneous. This type of injection is most typically performed in the arm or leg muscles. In some methods, agents are injected directly into a particular tissue where deposits have accumulated, for example intracranial injection.

The present regimes can be administered in combination with another agent effective in treatment or prophylaxis of the disease being treated. For example, in the case of Parkinson's disease, immunotherapy against alpha synuclein WO/2008/103472, Levodopa, benzaseride, carbidopa, dopamine agonists, non-ergot dopamine agonists, catechol-O-methyl ("COMT") inhibitors such as, for example, entacopone or tolcopone, monoamine oxidase ("MAO") inhibitors, such as, for example, rasagaline, amantadine, or anticholinergic agents can be used in combination with the present regimes.

An effective dosage of any of the pharmaceutical formulations described in greater detail below can be administered to therapeutically or prophylactically treat a human patient having or at risk for a synucleinopathy. Some of the formulations described below can be added to an infusion bag suitable for intravenous administration to a patient, for example for administration every four weeks. Some patients have been diagnosed with Parkinson's disease. The formulations described herein can be administered at a dose of about 0.3 mg/kg, about 1 mg/kg, about 3 mg/kg, about 10 mg/kg or about 30 mg/kg humanized 9E4 drug substance. In some patients, the dose may be further adjusted according to tolerance, safety, pharmacokinetics, efficacy and other parameters that may be determined empirically.

VIII. Formulations

Formulations (also known as pharmaceutical compositions) of the invention comprise an antibody (e.g., a chimeric, veneered or humanized version of murine 9E4 (ATCC Accession Number PTA-8221)) or antigen binding fragment thereof, a buffer, one or more sugars and/or polyols and a surfactant, and have a pH within the range from about 5 to about 7.5. The formulations can be prepared for storage in liquid form or in lyophilized form. When stored in lyophilized form, the formulations can be reconstituted with a liquid (e.g., sterile water) to the concentrations and properties described herein. When a lyophilized composition is said to be reconstitutable by adding water to generate a formulation of specified component concentrations and pH, it is meant that the lyophilized formulation can be so reconstituted simply by addition of water (i.e., without supplying additional amounts of components or adding acid or base to change the pH). The concentrations and properties of a prelyophilized liquid formulation can also be in accordance with those described below if the lyophilized formulation is reconstituted to the same volume as the formulation prelyophilization. If the volume is different, then concentrations of formulations should be adjusted proportionally. For example, if the reconstituted volume is half the prelyophilization volume, then the concentrations of components in the prelyophilization formulation should be half the concentrations in the reconstituted formulation.

Optionally, 9E4 antibody purified from a CHO cell culture is resuspended in a formulation as described below, temporarily frozen for storage prelyophilization, lyophilized, and reconstituted with water to the same concentrations as prelyophilization. Such a formulation should preferably stabilize the antibody throughout freezing, lyophilization, storage, and reconstitution as well as being suitable for parenteral administration. In an exemplary work flow, purified antibody is resuspended at about 40 mg/ml in Formulation 3 (Table 10) and stored frozen at −40 C in bags. Bags are thawed at room temperature for 3 hours and the contents are pooled. The formulation is sterile filtered through a 0.2 micron sterile filer. Vials are filled with 5.4 ml of the formulation and lyophilized. Lyophilized vials are stored at 2-8 C. Lyophilized vials are reconstituted by adding sterile water (e.g., approximately 5.0 to 5.4 ml sterile water, depending on the formulation). 5 ml of the reconstituted product is then added into the port of an IV bag containing 20-100 ml of normal saline, lactated Ringers solution, or 5% dextrose solution or the like for intravenous infusion into a patient.

Some formulations include a bulking agent, which may or may not be the same as the sugar/polyol component. Typically, the formulations are sterile, for example, as accomplished by sterile filtration using a 0.2 μm or a 0.22 μm filter. Some formulations have a bioburden of ≤ about 3 CFU/30 mL. Some formulations contain ≤ about 0.1 EU/mg of bacterial endotoxins. The formulations of the invention are also generally stable by low to undetectable levels of fragmentation and/or aggregation as further defined below on freezing and thawing. Still other formulations are stable following reconstitution of a lyophilized cake for at least three months at 40 degrees Celsius. In some formulations, less than about 10% of the antibody is present as an aggregate in the formulation. In some formulations, less than or equal to about 5% of the antibody is present as an aggregate in the formulation.

In some formulations, the antibody is present at a concentration within the range from about 5 mg/mL to about 100 mg/mL. In some formulations, the antibody is present at a concentration within the range from about 5 mg/mL to about 50 mg/mL. In some formulations, the antibody is present at a concentration within the range from about 25 mg/mL to about 50 mg/mL. For example, the antibody may be present at a concentration of about 35-45 mg/ml or about 40 mg/mL. The antibody may be present in a sterile liquid dosage form of about 50 mg/vial to about 500 mg/vial, or greater. The antibody may be present in a lyophilized dosage form of about 40 mg/vial to about 500 mg/vial. For example, the antibody may be present in a sterile liquid or lyophilized dosage form of about 250-350 mg/vial or about 200 mg/vial.

Antibodies used in the disclosed formulations can be coupled with a therapeutic moiety, such as a cytotoxic agent, a radiotherapeutic agent, an immunomodulator, a second antibody (e.g., to form an antibody heteroconjugate), or any other biologically active agent that facilitates or enhances the activity of the formulated antibody (e.g., chimeric, veneered or humanized 9E4). Representative therapeutic moieties include agents known to be useful for treatment, management, or amelioration of a Lewy body disease or symptoms of a synucleinopathy.

The formulated antibody can comprise any of the chimeric, veneered or humanized versions of antibody 9E4 described above. For example, the antibody can comprise a light chain variable region comprising the three Kabat CDRs of SEQ ID NO: 4 and a heavy chain variable region comprising the three Kabat CDRs of SEQ ID NO: 11. The formulation can include an antibody comprising a light chain variable region having an amino acid sequence comprising any one of SEQ ID NO: 3, SEQ ID NO: 4, or SEQ ID NO: 5, and/or a heavy chain variable region having an amino acid sequence comprising any one of SEQ ID NO: 8, SEQ ID NO: 9, SEQ ID NO: 10, or SEQ ID NO: 11. Some formulations include an antibody comprising a light chain variable region having the amino acid sequence comprising SEQ ID NO: 5. Some formulations include an antibody comprising a heavy chain variable region having the amino acid sequence comprising SEQ ID NO: 10. For example, the formulated antibody can comprise a light chain having the amino acid sequence comprising SEQ ID NO: 5 and a heavy chain having the amino acid sequence comprising SEQ ID NO: 10.

Buffers are used in the disclosed formulations to achieve a suitable pH for the antibody, such as, for example, histidine, succinate, and citrate buffers. Some formulations have a pH within the range from about 5.5 to about 7, for example, a pH of 5.5, 5.6, 5.7, 5.8, 5.9, 6.0, 6.1, 6.2, 6.3, 6.4, 6.5, 6.6, 6.7, 6.8, 6.9, or 7.0. Some formulations have a pH of between about 5.5 to about 6.5. Some formulations have a pH of about 6.0 and other formulations have a pH of about 6.5. In some formulations, citrate buffer or succinate buffer is present at a concentration within the range from about 10 mM to about 30 mM, for example, at a concentration of about 15-25 mM or about 20 mM. Some citrate buffers comprise sodium citrate dehydrate and citric acid monohydrate at a concentration within the range from about 15 mM to about 20 mM and a range from about 2 mM to about 6 mM, respectively.

Suitable sugars and/or polyols for the formulations include trehalose, sucrose, mannitol, or a combination thereof. Sugars/polyols serves as bulking agents, lyoprotecting agent, and/or tonicity adjusting agents. For example, some formulations include trehalose present at a concentration within the range from about 220 mM to about 260 mM, sucrose present at a concentration within the range from about 220 mM to about 260 mM, or a mixture of sucrose present at a concentration within the range from about 20 mM to about 40 mM and mannitol present at a concentration within the range from about 200 mM to about 220 mM. Some formulations include trehalose present at a concentration of about 230 mM or 240 mM. Other formulations include sucrose present at a concentration of about 230 mM or 240 mM. Other formulations include a mixture of sucrose present at a concentration of about 50 mM and mannitol present at a concentration of about 200 mM. Another formulation includes a mixture of sucrose present at a concentration of about 28 mM and mannitol present at a concentration of about 212 mM. Some such formulations are characterized by an osmolality in the range of about 250-400, 300-400, or 300-350 mOsm/kg, such as, for example, 335 mOsm/kg.

Formulations preferably contain a surfactant to reduce antibody aggregation and absorption to surfaces. Suitable surfactants include polysorbate 20 (PS20) present at a concentration within the range from about 0.005% to about 0.05% by weight. PS20 protects against marked increases in aggregation or turbidity that would otherwise occur in formulations of 9E4 antibodies. The polysorbate 20 may be present at a concentration within the range from about 0.01% to about 0.05%. For example, the concentration can be 0.005%, 0.01%, 0.015%, 0.02%, 0.025%, 0.03%, 0.035%, 0.04%, 0.045%, or 0.05%. Alternatively, in some formulations, polysorbate 20 is present at a concentration within the range of about from about 0.05 g/L, 0.1 g/L, 0.15 g/L, 0.2 g/L, 0.25 g/L, 0.3 g/L, 0.35 g/L, 0.4 g/L, 0.45 g/L, or 0.5 g/L. Some formulations include polysorbate 20 at a concentration of 0.2 g/L (i.e., 0.163 mmol/L).

An exemplary formulation (liquid, prelyophilization or reconstituted after lyophilization) is characterized by a pH within the range from about 5.5 to about 7 and includes: (a) a chimeric, veneered, or humanized version of antibody 9E4, or a fragment thereof that specifically competes for binding to antigen with 9E4 at a concentration within the range from about 10 mg/ml to about 50 mg/ml; (b) a citrate buffer or succinate buffer present at a concentration within the range from about 10 mM to about 30 mM; (c) one or more sugars and polyols ("sugar/polyol") selected from trehalose present at a concentration within the range from about 220 mM to about 260 mM, sucrose present at a concentration within the range from about 220 mM to about 260 mM, and a mixture of sucrose present at a concentration within the range from about 20 mM to about 40 mM and mannitol present at a concentration within the range from about 200 mM to about 220 mM; and (d) polysorbate 20 present at a concentration within the range from about 0.005% to about 0.05% by weight. For example, the formulation can include: (a) an antibody comprising a light chain having the amino acid sequence set forth as SEQ ID NO: 29 and a heavy chain comprising an amino acid sequence set forth as SEQ ID NO: 32, with or without the C-terminal lysine, and which is present at a concentration of about 40 mg/mL; (b) a citrate buffer at a concentration of about 20 mM; (c) trehalose at a concentration of about 230 mM; (d) polysorbate 20 at a concentration of about 0.02%; and a pH of about 6.0.

Some lyophilized formulations include: (a) a humanized version of antibody 9E4 or an antigen binding fragment thereof; (b) citrate; (c) trehalose; and polysorbate 20. The lyophilized formulation can include about 200 mg of the antibody. Some lyophilized formulations are capable of being reconstituted with sterile water. Some lyophilized formulations include 100-300 or 150-250 mg 9E4 antibody, 15-35 or 20-25 mg sodium citrate dehydrate, 1.65-2.75 or 2-2.3 mg citric acid monohydrate, 360-500 or 400-470 mg trehalose dehydrate, and 0.5 to 1.5 mg or 0.75 to 1.25 mg polysorbate 20. An exemplary lyophilized formulation includes 200 mg of a 9E4 antibody (e.g., humanized 9E4 antibody), 25 mg of sodium citrate dehydrate, 2.15 mg citric acid monohydrate, 435 mg trehalose dehydrate, and 1 mg polysorbate 20. Another exemplary lyophilized formulation includes 200 mg of a 9E4 antibody (e.g., humanized 9E4 antibody), 25 mg of sodium citrate dehydrate, 3.15 mg citric acid monohydrate, 435 mg trehalose dehydrate, and 1 mg polysorbate 20. Such formulations are preferably reconstituted to a volume of about 5 ml. Other lyophilized formulations include the same components in the same proportions as any disclosed in this paragraph but in different amounts (e.g., 400 mg antibody, 50 mg sodium citrate, 4.3 mg citric acid monohydrate, 870 mg Trehalose dehydrate, and 2 mg polysorbate 20).

Lyophilized formulations are preferably reconstituted to an antibody concentration of about 30-50 or 35-45 mg/mL, preferably about 40 mg/mL; (b) a citrate buffer present at a concentration of about 10-30 or 15-25 mM, preferably about 20 mM; (c) trehalose present at a concentration of about 160-330 or 200-260 mM preferably about 230 mM; (d) polysorbate 20 present at a concentration of about 0.1-0.3 or 0.15 to 0.25 g/L, preferably about 0.2 g/L; and (e) a pH of about 5.5-6.5, preferably about 6.0.

Liquid or reconstituted lyophilized formulations are preferably substantially isotonic, implying an osmolality of about 250-350 mOsm/kg water. Some formulations have an osmolality of about 335 mOsm/kg. Some formulations have an osmolality of 270-300 mOsm/kg. Liquid or reconstituted lyophilized formulations can also be hypertonic >350 mOsm/kg water or hypotonic (<250 mOsm/kg water).

Some lyophilized formulations appear as a white to yellowish powder. Some liquid or reconstituted lyophilized formulations appear as a solution practically free of foreign particles and may contain a few translucent, white to whitish product-typical particles. Some liquid or reconstituted lyophilized formulations have ≤ about 6,000 sub-visible particles ≥10 μm per vial (volume=5 ml) and/or ≤ about 600 sub-visible particles ≥25 μm per vial. Some liquid or reconstituted lyophilized formulations appear as colorless to slightly yellow (≤ reference solution BY3). Some liquid or reconstituted lyophilized formulations appear as clear to slightly opalescent (≤ reference suspension III).

Any of the formulations described can be made without pharmaceutical excipients, carriers or the like, other than those described as being components herein. Such a formulation can be described as consisting of the recited components, or consisting essentially of the recited components if insignificant amounts of other components not affecting the properties of the formulation are present. Formulations are preferably made under good manufacturing practices (GMP) approved or approvable by the FDA for preparation of drugs for administration to humans.

Antibodies used in the disclosed formulations can also be coupled with a detectable label, for example, as useful for diagnosing a synucleinopathy, for monitoring progression of a synucleinopathy, and/or for assessing efficacy of treatment. Antibodies formulated as described are particularly useful for performing such determinations in subjects having or being susceptible to a synucleinopathy such as Parkinson's disease, or in appropriate biological samples obtained from such subjects. Representative detectable labels that may be coupled or linked to a humanized 9E4 antibody include various enzymes, such as horseradish peroxidase, alkaline phosphatase, beta-galactosidase, or acetylcholinesterase; prosthetic groups, such streptavidinlbiotin and avidin/biotin; fluorescent materials, such as but umbelliferone, fluorescein, fluorescein isothiocynate, rhodamine, dichlorotriazinylamine fluorescein, dansyl chloride or phycoerythrin; luminescent materials, such as luminol; bioluminescent materials, such as luciferase, luciferin, and aequorin; radioactive materials, such as but not limited to iodine ($^{131}I$, $^{125}I$, $^{123}I$, $^{121}I$), carbon ($^{14}C$), sulfur ($^{5}S$), tritium ($^{3}H$), indium ($^{115}In$, $^{113}In$, $^{112}In$, $^{111}In$), and technetium ($^{99}Tc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, $^{97}Ru$, $^{68}Ge$, $^{57}Co$, $^{65}Zn$, $^{85}Sr$, $^{32}P$, $^{153}Gd$, $^{169}Yb$, $^{51}Cr$, $^{54}Mn$, $^{75}Se$, $^{113}Sn$, and $^{117}Tin$; positron emitting metals using various positron emission tomographies, nonradioactive paramagnetic metal ions, and molecules that are radiolabelled or conjugated to specific radioisotopes.

Therapeutic moieties and/or detectable substances may be coupled or conjugated directly to a murine, chimeric, veneered, or humanized 9E4 antibody, or indirectly, through an intermediate (e.g., a linker) using techniques known in the art. See e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radio labeled Antibody In Cancer Therapy", in Monoclonal Antibodies For Cancer Detection And Therapy, Baldwin et al. (eds.), pp. 303-16 (Academic Press 1985), and Thorpe et al., *Immunol. Rev.,* 1982, 62:119-58.

Antibodies used in the disclosed formulations also include modified forms of murine, chimeric, veneered, or humanized 9E4 antibodies, which have increased in vivo half-lives relative to the corresponding unmodified antibodies. Such modified forms may be prepared, for example, by glycosylation, acetylation, pegylation, phosphorylation, amidation, derivatization by known protecting/blocking groups, proteolytic cleavage, linkage to a cellular ligand or other protein. As one example, representative methods for antibody half-life extension are described in WO 02/060919.

The present invention encompasses antibody formulations having stability at 38° C.-42° C. (e.g., as assessed by high performance size exclusion chromatography (HPSEC)) for at least about 30 days, formulations having stability at 20° C.-24° C. for at least about 1 year, and formulations having stability at 2° C.-4° C. for at least about 3 years. Stability of lyophilized formulations is assessed for storage in the lyophilized state. A formulation is considered stable if, after incubation at one or more of these specified combinations of time and temperature, it meets the below definition for low to undetectable fragmentation and/or low to undetectable aggregation. More particularly, the disclosed formulations exhibit low to undetectable levels of antibody aggregation and/or fragmentation, or a low or undetectable increase in antibody fragmentation and/or aggregation above an initial level (e.g., less than about 10% aggregation). Some formulations exhibit ≤ about 5% combined aggregation and/or fragmentation. A formulation having low to undetectable levels of fragmentation contains at least about 80%, 85%, 90%, 95%, 98%, or 99%, of the total protein, for example, in a single peak as determined by high performance size exclusion chromatography (HPSEC), or in two peaks (one corresponding to each of the antibody heavy chains and antibody light chains) by reduced Capillary Gel Electrophoresis (rCGE), representing the non-degraded antibody, and containing no other single peaks having more than 5%, more than 4%, more than 3%, more than 2%, more than 1%, or more than 0.5% of the total protein each. A formulation having low to undetectable levels of aggregation contains no more than about 15%, no more than about 10%, no more that about 5%, no more than about 4%, no more than about 3%, no more than about 2%, no more than about 1%, or no more than about 0.5% aggregation by weight protein, as measured by high performance size exclusion chromatography (HPSEC). For example, in some formulations, less than about 10% of the anti-synuclein antibody is present as an aggregate. Stable formulations of the invention also show little or no loss of biological activity(ies) of a chimeric, veneered or humanized 9E4, having, for example, binding affinity measurable by ELISAs and/or additional functional assay, that is at least about 50%, 55%, 60%, 65%, 70%, 75%, 80%, 85%, 90%, 95%, 98%, or 99% of an initial measurable value. Some formulations have a binding affinity that is from about 60% to about 140% of an initial measurable value of the reference material.

IX. Preparation of Pharmaceutical Formulations

The present invention also provides methods of preparing pharmaceutical formulations. In one aspect of the invention, such a method comprises: (a) culturing mammalian cells having stably incorporated into their genome nucleic acids encoding the light and heavy chains of murine antibody 9E4 (ATCC Accession Number PTA-8221), or of a chimeric, veneered, or humanized versions thereof, so that the cells secrete the antibody into the cell culture media; (b) purifying the antibody from the cell culture media; and (c) preparing any of the formulations described above.

The preparation of a pharmaceutical formulation can include the additional step of evaluating at least one property of an antibody in the formulation, selected from the group consisting of physical stability, chemical stability, and biological activity.

For example, mammalian cells can be cultured for the production of antibodies, wherein the mammalian cells have stably incorporated into their genomes nucleic acids encoding the light and heavy chains of a humanized 9E4 antibody. Mammalian cells useful for this purpose include host cells having stably incorporated into their genomes a nucleic acid sequence encoding an antibody light chain set forth as SEQ ID NO: 29 and an antibody heavy chain set forth as SEQ ID NO: 31 or 32.

For the production of antibodies, the disclosed nucleic acids are included in a vector. In some examples, the vector contains the nucleic acid encoding murine 9E4 antibody, or a chimeric, veneered, or humanized version thereof, operably linked to a suitable control sequence capable of effecting the expression of the DNA in a host cell. Such control sequences include a promoter to effect transcription (e.g., a constitutive promoter or inducible promoter as known in the art), an optional operator sequence to control such transcription, a sequence encoding suitable mRNA ribosome binding sites, enhancers, polyadenylation signals, and sequences to control the termination of transcription and translation. The vector may be a plasmid, a phage particle (e.g., a viral vector such as adenovirus, adeno-associated-virus, retrovirus, herpes virus, vaccinia virus, lentivirus, poxvirus and cytomegalovirus vectors), or simply a genomic insert. Once transformed into a suitable host, the antibody nucleic acids may integrate into the genome of the host, or the vector may replicate and function independently of the host genome.

The disclosed nucleic acids are included in a vector either singly or in combination (e.g., a combination of a nucleic acid encoding an antibody light chain and a nucleic acid encoding an antibody heavy chain).

Host cells useful for preparing antibody formulations of the invention include mammalian cells, including cells of human origin, human embryonic kidney cells, monkey kidney cells, baby hamster kidney (BHK) cells, Chinese hamster ovary cells (CHO) cells, mouse sertoli cells, human cervical carcinoma (HeLa) cells, canine kidney cells, human lung cells, human liver cells, mouse mammary tumor cells, and NS0 cells.

Alternatively, a chimeric, veneered, or humanized 9E4 antibody can be prepared by chemical synthesis and then used in the disclosed formulations.

Antibodies used to prepare the disclosed formulations are typically isolated or purified, i.e., substantially free of cellular material or other contaminating proteins from the cells in which they are produced, or substantially free of chemical precursors or other chemicals when chemically synthesized. For example, an antibody that is substantially free of cellular material includes preparations of the antibody having less than about 30%, 25%, 20%, 15%, 10%, 8%, 5%, 2%, 1%, 0.5%, 0.1%, or less (by dry weight) of contaminating protein. When an antibody is recombinantly produced, it is also substantially free of culture medium such that culture medium represents less than about 30%, 25%, 20%, 15%, 10%, 8%, 5%, 2%, 1%, 0.5%, 0.1%, or less, of the volume of the protein preparation. When an antibody is produced by chemical synthesis, it is preferably substantially free of or separated from chemical precursors or other chemicals involved in the synthesis of the protein. Accordingly, such antibody preparations have less than about 30%, 25%, 20%, 15%, 10%, 8%, 5%, 2%, 1%, 0.5%, 0.1%, or less (by dry weight) of chemical precursors or compounds other than the antibody drug substance. For example, some preparations of the antibody drug substance have the following purity as determined by the following assays: protein A ELISA (≤ about 25 ng/mg), CHOP ELISA (≤ about 100 $U^2$/mg), IGF-1 ELISA (≤ about 1 ng/mg), insulin ELISA (≤ about 1 ng/mg), and DNA qPCR (≤ about 3 pg/mg protein). Some preparations of the antibody drug substance have a bioburden of ≤ about 10 CFU/mL. Some preparations of the antibody drug substance contain ≤ about 0.5 EU/mg of bacterial endotoxins. Purification of recombinantly expressed antibody can utilize any of a number of methods known in the art, such as, for example, affinity chromatography, acid treatment, depth filtration, anion exchange chromatography, cation exchange chromatography, nanofiltration, ultrafiltration, dialysis and diafiltration.

The purified antibody drug substance can be adjusted to a solution comprising any of the formulations described herein, diluted to the desired concentration and stored until ready for use. Optionally, the formulation can be stored in concentrated form until ready for use.

Liquid formulations can be stored in frozen form, under refrigeration, or at room temperature, depending on their stability profile, which can be determined empirically. In some instances a further filtration step is applied. Some of the formulations described herein may be lyophilized and stored in powder form. Lyophilized formulations can be stored in frozen form, under refrigeration or at room temperature, depending on their stability profile, which can be determined empirically. For example, the lyophilized formulations can be stored at a temperature of about 2° C. to 8° C. In such cases, the formulation would be reconstituted prior to administration to a patient to yield a liquid formulation having the antibody and excipients present in the concentrations described herein. In some cases, the formulation is reconstituted in sterile water. In some cases, the formulation is reconstituted and added to an infusion bag for administration to the patient. The reconstituted formulation can be stored under refrigeration or at room temperature prior to administration to a patient for a time consistent with the stability profile. Lyophilization and reconstitution techniques are known in the art and described in the Examples.

Either a liquid formulation or reconstituted lyophilized formulation can be added to infusion bag containing a diluent such as normal saline or Ringer's solution before administration to the patient. The volume of the infusion bag is usually relatively large (e.g., 50 ml to 1 L, or 100-500 ml) compared with the volume of the liquid formulation or constituted lyophilized formulation (e.g., 1-10 ml). Several liquids can be used in the infusion bag, such as normal saline, lactated Ringers solution, or 5% dextrose solution, each of which is substantially isotonic. In an exemplary regime about 5 ml of liquid or reconstituted lyophilized formulation is injected through the port of a 100-ml bag of normal saline and administered by iv infusion over a period of about an hour at a flow rate of about 1.75 ml/min.

Thus, the present invention also encompasses pharmaceutical products comprising lyophilized antibody drug substance and instructions for reconstitution and use. Some pharmaceutical products comprise: (a) a vial comprising about 40 to about 200 mg antibody in powder form; and (b) instructions for reconstitution of the antibody. An exemplary pharmaceutical product includes: (a) a vial comprising, in powder form, about 200 mg antibody, about 25 mg sodium citrate dehydrate, about 3.15 mg citric acid monohydrate, about 435 mg trehalose dehydrate and about 1 mg polysorbate 20; (b) instructions for reconstitution; and (c) instructions for preparing the reconstituted formulation for infusion, wherein (i) the antibody comprises a light chain comprising an amino acid sequence set forth as SEQ ID NO: 29 and a heavy chain comprising an amino acid sequence set forth as SEQ ID NO: 32 with or without the C-terminal lysine; and (ii) the reconstitution instructions require reconstitution with water for injection to an extractable volume of 5 mL.

EXAMPLES

The following examples have been included to illustrate modes of the invention. Certain aspects of the following examples are described in terms of techniques and procedures found or contemplated by the present co-inventors to work well in the practice of the invention. In light of the present disclosure and the general level of skill in the art, those of skill appreciate that the following examples are intended to be exemplary only and that numerous changes, modifications, and alterations may be employed without departing from the scope of the invention.

Example 1: Preparation of the Expression Vector

The humanized 9E4-specific sequences of the variable regions of both heavy and light chain (SEQ ID NOS: 32 and 29, respectively) were subcloned into expression vectors which contain genetic elements allowing for the enrichment of high-producers (e.g., transcription enhancing element (TS), polyadenylation signals, neomycin phosphotransferase mutant).

Using the plasmid pCET Hu9E4VLv3.hCK as a template, the variable region of the light chain was isolated by PCR, introducing at the 5' ends of the fragments an EcoRV restriction site and at the 3' ends a KpnI restriction site for subcloning into the vectors pBI-60 and pBI-90 digested with the same restriction enzymes. These vectors contained the genomic constant region of a human kappa chain. In addition, the vectors pBI-60 and pBI-90 encode the attenuated selection marker neomycin phosphotransferase for enrichment of high producers during selection. pBI-60 encodes the F240I mutant of neomycin phosphotransferase and vector pBI-90 encodes the D227V mutant.

Using the plasmid pCET Hu9E4VHv3.hIgG1 as a template, the variable region of humanized 9E4 heavy chain was isolated by PCR, introducing at the 5' ends an MfeI restriction site and at the 3' ends a BlpI restriction site for subcloning. The variable region was cloned into the MfeI and BamHI digested eukaryotic expression vector pBI-61, containing the genomic constant regions of human IgG1 of G1m(3) allotype. The vector encodes the selectable marker dihydrofolate reductase (DHFR) from hamster.

Example 2: Production of Humanized 9E4 Antibody

The plasmids pBI-61/9E4 HC and pBI-60/9E4 LC were co-transfected into Chinese Hamster Ovary (CHO) cells pre-adapted to serum-free growth media. The cells were grown in chemically defined media without any bovine-derived components. The culture media for established cell lines was as follows:

Preinocculation Medium:

| Component | BI-Mat. Nr. | Conc./L |
|---|---|---|
| WFI | 27259 | 0.80 L |
| GMBI 211 | 80264 | 11.90 g |
| NaHCO3 | 23904 | 4.50 g |
| Supplement III | 70994 | 1.80 g |

-continued

| Component | BI-Mat. Nr. | Conc./L |
|---|---|---|
| Insulin Stock sol No2 pharma | 65422 | 2 mL |
| Glucose anhydrous | 29603 | 5.0 g |
| L-Glutamine | 23516 | 1.45 g |
| Supplement I | 71455 | 2.50 g |
| Succinic acid | 42949 | 1.50 g |
| WFI | 27259 | 0.176 L |
| 40% NaOH | 26181 | as needed |

Preparation of Preinocculation Medium:
 1) WFI starting volume 80% of total volume; temperature at start 28 to 35° C.
 2) Add components one by one, according to the list (above), as soon as each previous component is dissolved completely.
 3) WFI rest volume 0.176 L/L medium
 4) Prior to filtration, adjust pH to between 7.00 and 7.20
 5) Prior to filtration, osmolarity is 280 to 320 mOsmol/kg
Post-Inoculation Additions:
 Nutrient Feed Medium
 3% Glutamine solution
 Glucose solution (500 g/L)
 1 M Sodium Carbonate solution
 2% Antifoam emulsion
Nutrient Feed Medium:

| Component | BI-Mat. Nr. | Conc./L |
|---|---|---|
| WFI | 27259 | 0.70 L |
| GM BI 220 | 80265 | 76.60 g |
| Sodium Bicarbonate | 23904 | 1.50 g |
| Supplement III | 70994 | 0.56 g |
| Insulin Stock sol No2 pharma | 65422 | 10 mL |
| Glucose anhydrous | 29603 | 83.40 g |
| Supplement II | 71456 | 4.95 g |
| L-Cysteine x HCl x H2O | 55946 | 2.60 g |
| WFI | 27259 | 0.179 L |
| 40% NaOH | 26181 | as needed |

Preparation of Nutrient Feed Medium:
 1) WFI starting volume 70% of total volume; temperature at start 30 to 40° C.
 2) Add components one by one, according to the list (above), as soon as each previous component is dissolved completely
 3) WFI rest volume 0.179 L/L medium
 4) Prior to filtration, adjust pH to between 6.90 and 7.10
 5) Prior to filtration, osmolality is 1185 to 1585 mOsmol/kg
Medium Filtration:
 Prefilter—0.2 μm filters
 Final filter—0.1 μm filters
Antibody was pooled from stable transfected cells from which the production cell line was ultimately derived. The pool-derived material was purified by protein A-affinity chromatography and other purification techniques, as described below.

Example 3: Antibody Purification

Protein A is a bacterial protein used for affinity purification of humanized, veneered, or chimeric 9E4 antibodies. Protein A chromatography typically involves passage of clarified cell culture supernatant over the column at pH 6-8, under which conditions the antibodies bind and unwanted components, such as host cell proteins, cell culture media components, and putative viruses, flow through the column. An optional intermediate wash step may be carried out to remove non-specifically bound impurities from the column, followed by elution of the product at pH 2.5-4. Types of Protein A resins classified based on their resin backbone composition include glass or silica-based, e.g., Prosep vA, Prosep vA Ultra (Millipore); agarose-based, e.g., Protein A Sepharose Fast Flow, MabSelect (GE Healthcare); and organic polymer based, e.g., polystyrene-divinylbenzene Poros A and MabCapture (Applied Biosystems). Several elution buffer components such as acetic acid, citric acid, phosphoric acid, arginine HCl and glycine HCl can be used.

Viruses can be removed by treatment at low pH or filtration among other methods. Current virus-retentive filters are ultrafilters or microfilters with very small pores. Virus filtration membranes are made from hydrophilic polyethersulfone (PES), hydrophilic polyvinylidene (PVDF) and regenerated cellulose.

Depth filters are used in the clarification of cell culture broths, to maintain capacity on membrane filters or to protect chromatography columns or virus filters. Depth filters are typically made of cellulose, a porous filter-aid such as diatomaceous earth and an ionic charged resin binder. Depth filters can employ both size exclusion and adsorptive binding to effect separation.

Ion exchange chromatography uses positively or negatively charged resins to bind proteins based on their net charges in a given buffer system. Conditions (e.g., pH and ionic strength) can be determined that bind and release the target antibody with a high degree of specificity. Conversely, conditions can be found that bind nearly all other sample components except antibodies. Anion exchange chromatography uses a positively charged group (weakly basic such as diethylamino ethyl, DEAE or dimethylamino ethyl, DMAE; or strongly basic such as quaternary amino ethyl, Q or trimethylammonium ethyl, TMAE or quaternary aminoethyl, QAE).

Cation exchange chromatography uses a resin modified with negatively charged functional groups. They can be strong acidic ligands such as sulphopropyl, sulfoethyl and sulfoisobutyl groups or weak acidic ligand such as carboxyl group. Cation exchange chromatography has been applied for purification processes for many mAbs with pI values ranging from neutral to basic. The antibody is bound onto the resin during the loading step and eluted through either increasing conductivity or increasing pH in the elution buffer. Negatively charged process-related impurities such as DNA, some host cell protein, leached Protein A and endotoxin are removed in the load and wash fraction. Cation exchange chromatography can also separate deamidated products, oxidized species and N-terminal truncated forms, as well as high molecular weight species from the desired antibody. Binding of antibodies on cation exchange resins depends on pH and conductivity, and resin type. SP Sepharose FF and SP Sepharose XL are two common commercially available resins.

Ultrafiltration is a pressure-driven membrane process for antibody concentration and buffer exchange. Ultrafiltration is a size-based separation in which species larger than the membrane pores are retained and smaller species pass through freely. Separation in ultrafiltration is achieved through differences in the filtration rates of different components across the membrane under a given pressure driving force. Buffer exchange is achieved using a diafiltration mode in which buffer of the final desired composition is added to the retentate system at the same rate in which filtrate is removed, thus maintaining a constant retentate volume. Ultrafiltration with membrane pores ranging from 1 to 20 nm can provide separation of species ranging in molecular weight from 500 daltons to 1,000 kilodaltons.

9E4 antibody product was captured from the harvest filtrate by rProtein-A affinity chromatography using Mab-Select resin from GE Healthcare. The product binds to the Protein A resin at neutral pH and is eluted in an isocratic mode with 100 mM sodium acetate at pH 3.0. The majority of host cell impurities and cell culture medium components are reduced during this step. A separate wash step with half PAIN buffer (500 mM NaCl, 1.34 mM KCl, 4 mM $Na_2HPO_4 \times 2H_2O$, 0.735 mM $KH_2PO_4 \times 2H_2O$, 0.125% PVP=kollidon 17, 7.5% isopropanol, 4.3 mM NaOH, 250 mM L-arginine-HCL, pH 7.4, conductivity 45 mS/cm) was implemented to remove components still remaining on the column and to minimize turbidity in the neutralized AT product pool. The protein A step was performed in a maximum of three cycles by splitting the harvest pool in similar loads. The column was equilibrated to pH 7.4±0.2 and conductivity 16±3 mS/cm with 1.47 mM KH2PO4× 2H2O, 8.03 mM Na2HPO4×2H2O 137 mM NaCl, 2.68 mM KCl to remove storage solution and to prepare the column for loading. The column was then loaded with a maximum of 30 g/L harvest filtrate, washed (3 buffers, 3 Column Volumes each), and eluted. After elution, the column is stripped by means of 0.1M phosphoric acid and equilibrated for the next cycle or fully regenerated and stored, if the subsequent cycle is performed the next day. Full regeneration with 0.1M phosphoric acid (strip), 6M urea and 1M acetic acid is performed after the last cycle.

The pooled and 0.2 µm filtered MabSelect product pool is adjusted to pH 3.5 with 1 M acetic acid (stirred) and incubated for 60-70 minutes at room temperature for viral inactivation (without stirring). Neutralization under stirring is performed by addition of 1 M tris base to pH 5.50±0.20.

The acid treated product pool is immediately passed over to the following depth filtration step. The depth filtration by Cuno Zeta Plus 60ZA is a step for the removal of turbidities. The virus inactivated product pool is filtered by a two-stage filtration process consisting of the above mentioned depth filter material in series with a 0.2 µm PES membrane filter.

The depth filtration product pool was further purified by anion exchange chromatography (AEX) using Q-Sepharose Fast Flow resin from GE Healthcare in a flow-through mode. The AEX step reduces residual host cell DNA and removes viruses. The column was equilibrated to pH 7.50±0.20 and conductivity 8.0±1.0 mS/cm with Q equilibration buffer (42.8 mM trometamol-HCl 7.2 mM tris base, 39 mM NaCl) to remove the storage solution and to prepare the column for loading. During loading the product flowed through the column while impurities bound to the resin. After loading/ eluting, the column was washed with Q equilibration buffer to recover the product remaining in the mobile phase on the column. After product recovery the column was regenerated and finally stored.

The adjusted Q-Sepharose product pool was further purified by cation exchange chromatography (CEX) using Poros HS50 from Applied Biosystems. The product bound to the column under low salt conditions (36.2 mM $CH_3COONa \times 3H_2O$, 13.8 mM $CH_3COOH$, 58.5 mM NaCl, pH 5.1, conductivity 8 mS/cm) and was then eluted in an isocratic mode under high salt conditions (38 mM $CH_3COONa \times 3H_2O$, 12 mM $CH_3COOH$, 228 mM NaCl, pH 5.1, conductivity 25.5 mS/cm). An additional wash step with medium salt amount (37.2 mM $CH_3COONa \times 3H_2O$, 12.8 mM $CH_3COOH$, 102.5 mM NaCl, pH 5.1, conductivity 13.5 mS/cm) was implemented to remove contaminants such as host cell proteins, high molecular weight product variants and leached Protein A. The CEX step was performed for a maximum of 2 cycles. In such instances, the adjusted AEX pool is separated into 2 equal volumes and processed individually on the CEX column.

The virus filtration (VF) provides a second orthogonal method specifically for the removal of virus particles and was designed to remove particles that are larger than 20 nm (e.g. Parvovirus). The virus filtration was accomplished via a pressure transfer of the Poros HS50 product pool through 0.1 µm prefilter and a viral filter (Planova 20 N, Asahi Kasei) in series, with a 1.0 bar pressure drop across the nanofilter. Integrity testing of the virus filter was performed pre-use (leak test) and post-use (leak test and gold particle test).

The nano-filtered product pool was concentrated to ~20 g/L (UF1) and is then diafiltered at constant volume against ≥6 volumes of diafiltration buffer (17 mM $C_6H_5Na_3O_7 \times 2$ $H_2O$, 3 mM $C_6H_8O_7 \times H_2O$, pH 6, conductivity 4 mS/cm). After diafiltration the pool was concentrated to ~75 g/L (UF2). Finally, the retentate was removed from the UF/DF system by flushing with diafiltration buffer to a concentration of ~52 g/L (="30 kD product pool").

The 30 kD product pool was mixed in a ratio 4+1 with 5-fold trehalose/Tween20 (Polysorbate 20) spike buffer (17 mM $C_6H_5Na_3O_7 \times 2$ $H_2O$, 3 mM $C_6H_8O_7 \times H_2O$, 1150 mM trehalose×2$H_2O$, 1 g/L polysorbate 20, pH 5.9, conductivity 1.0 mS/cm) and diluted with formulation buffer (17 mM $C_6H_5Na_3O_7 \times 2$ $H_2O$, 3 mM $C_6H_8O_7 \times H_2O$, 230 mM trehalose×2$H_2O$, 0.2 g/L polysorbate 20, pH 6.0, conductivity 3.30 mS/cm) to get a protein concentration of 40.0±2.0 g/L.

The bulk material was filtered through a 0.2 µm pool filter and a 0.2 µm bag filter connected in series. An additional pre-filter to the 0.2 µm filter may be implemented for particle removal. The 0.2 µm pool filter was tested for integrity. If the pool filter fails the testing, each bag filter is tested separately for integrity.

Example 4: Formulation Development

Throughout this example, humanized 9E4 antibody having the light chain sequence of SEQ ID NO: 29 and the heavy chain sequence of SEQ ID NO: 32 was used.

Physicochemical Characterization.

To facilitate selection of potential formulation components, the termal characteristics of humanized 9E4 antibody were determined. Differential scanning calorimetry ("DSC"), right angle light scattering ("RALS") and intrinsic fluorescence ("IF") techniques were used in the analysis. Purified antibody was first heated from 10° C. to 71° C., then cooled from 71° C. to 10° C., then heated again from 10° C. to 83° C., then cooled again from 83° C. to 10° C., and finally heated again from 10° C. to 95° C. The DSC thermogram revealed two transitions, the first at 71° C. and the second at 83° C. See FIG. 1. The transition of 71° C. was reversible under the experimental conditions. The RALS and IF thermograms revealed a single transition at an intermediate temperature.

pH Optimization.

Figure 2:
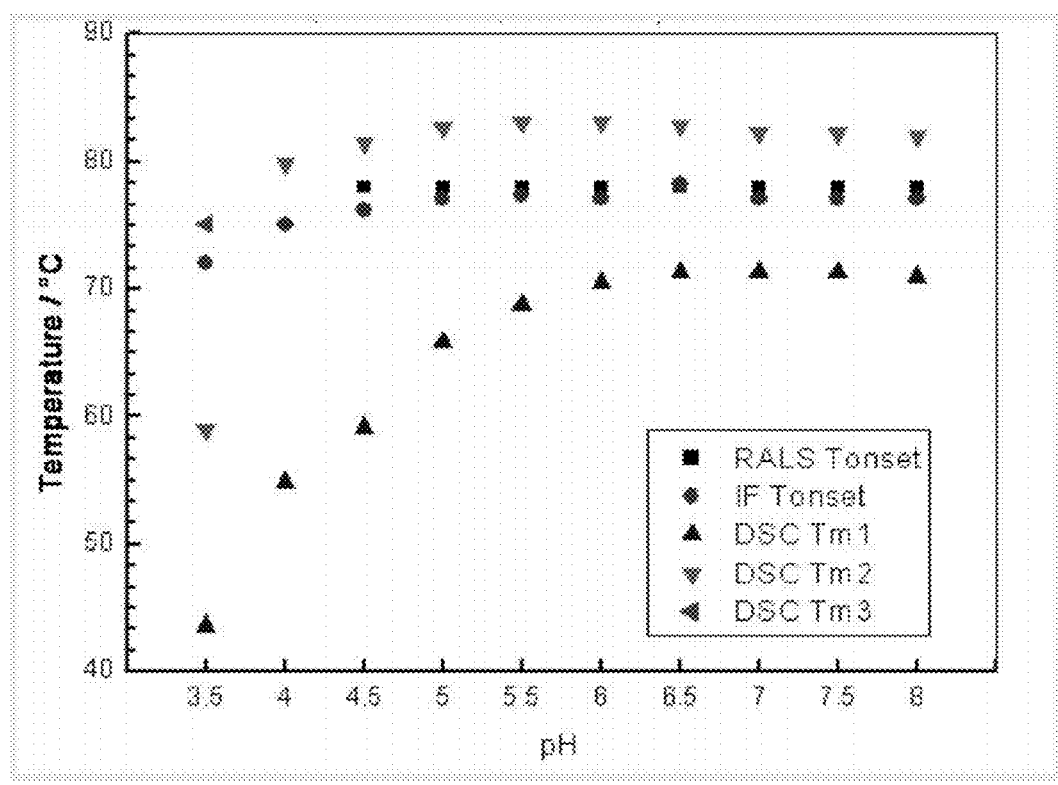
FIG. 2 is a graph depicting the transition temperatures for humanized 9E4 antibody (version H3L3) as a function of pH. The different symbols show the transition temperature as determined by RALS, IF, and DSC. Two or three DSC transition temperatures were observed at each pH, and each is presented with a distinct symbol.

The stability of humanized 9E4 was next analyzed in a mixed buffer system having pH values ranging from 3.5 to 8.0. Again, DSC, RALS, and IF techniques were used in the analysis. As before, two transitions were detected in the DSC thermogram (with the exception of a third transition detected at pH 3.5) and a single intermediate transition was detected in the RALS and IF termograms. The first thermal transition in the DSC analysis increased with increasing pH until a pH of 6.5, when it leveled off at about 71° C. (Table 4, below, & FIG. 2). The second thermal transition in the DSC analysis peaked at around 83° C., between a pH of 5.0 and 6.5. The thermal transition in the RALS analysis remained at about 77° C. for the pH range of 4.5-8.0, and the IF thermal transition varied between 75° C. and 77° C. over the same pH range (FIG. 2). Based on the results, a pH range of 5.5 to 7.0 was determined to provide the most stability for humanized 9E4 antibody.

TABLE 4

DSC Thermal Transition Peaks for Humanized 9E4 as a Function of pH

| pH | Tm1 (° C.) | Tm* (° C.) | Tm2 (° C.) |
|---|---|---|---|
| 3.5 | 43.6 | 59.0 | 75.1 |
| 4.0 | 54.9 | — | 79.8 |
| 4.5 | 59.2 | — | 81.4 |
| 5.0 | 65.9 | — | 82.7 |
| 5.5 | 68.8 | — | 83.1 |
| 6.0 | 70.6 | — | 83.0 |
| 6.5 | 71.3 | — | 82.8 |
| 7.0 | 71.3 | — | 82.3 |
| 7.5 | 71.3 | — | 82.2 |
| 8.0 | 71.0 | — | 82.0 |

Buffer Selection.

Based on the the pH-dependent stability results for humanized 9E4 antibody, buffer systems were identified which are pharmaceutically acceptable for parenteral use and could provide sufficient buffer capacity in the pH range between pH 5.5 and 7.0. These buffer systems included 20 mM citrate buffer (pH 5.5; 6.0), 20 mM histidine buffer (pH 6.0; 6.5; 7.0), and 20 mM succinate buffer (pH 6.5). The thermal stability of humanized 9E4 antibody in the 20 mM succinate and 20 mM histidine buffers was tested by DSC, RALS, and IF. As determined by DSC, humanized 9E4 antibody in the citrate buffer, at a pH between 5.5 and 6.0, showed a significantly higher second thermal transition (Tm2) as compared to humanized 9E4 antibody in the histidine buffer (Table 5, below). Conversely, humanized 9E4 antibody in the histidine buffer, at a pH between 6.5 and 7.0, showed a higher first thermal transition (Tm1) as compared to humanized 9E4 antibody in the citrate buffer (Table 5). No thermal transitions were detected for the histidine buffered antibody using the RALS technique. The citrate buffered antibody, however, exhibited a thermal transition at 78° C. at pH 5.5 and 6.0.

Succinate buffered humanized 9E4 antibody (pH 6.5) was also analyzed by DSC and RALS and the results compared to citrate buffered (pH 6.5) and histidine buffered (pH 6.5) antibody. For the DSC analysis, the second thermal transition (Tm2) in the citrate and succinate buffers was approximately 1° C. higher than in the histinde buffer, indicating a slightly higher stability of the protein under the tested conditions. Comparable transition temperatures were detected by RALS for the succinate and citrate buffers at pH 6.5.

Based on these findings 20 mM citrate (pH 6.0) and 20 mM succinate (pH 6.5) buffers were selected for use in producing a lyophilized drug product and testing its long-term stability.

TABLE 5

DSC Thermal Transition Peaks for Humanized 9E4 as a Function of Buffer

| Buffer | Tm1 (° C.) | Tm2 (° C.) |
|---|---|---|
| Citrate (pH 5.5) | 68.8 | 83.4 |
| Citrate (pH 6.0) | 70.2 | 83.2 |
| Histidine (pH 6.0) | 68.9 | 81.9 |
| Histidine (pH 6.5) | 71.3 | 81.9 |
| Histidine (pH 7.0) | 71.4 | 82.5 |
| Succinate (pH 6.5) | 71.8 | 82.8 |

Sugar/Polyol Selection.

With the goal of increasing stability of humanized 9E4 antibody in a freeze dried formulation, the impact of sugars and polyols on the thermal stability of the antibody was analyzed. The sugars/polyols evaluated included trehalose, sucrose, or a mixture of sucrose and mannitol. 240 mM trehalose, 240 mM sucrose, and 50 mM sucrose/200 mM mannitol were each added to 20 mM succinate (pH 6.5), 20 mM histidine (pH 6.5), and 20 mM citrate (pH 6.5) buffers. The stability of the humanized 9E4 antibody was then evaluated by DSC for each of the formulations. The DSC results revealed that the the various sugars/polyols shifted the first and second thermal transitions to higher temperatures, indicating a stabilizing effect (Table 6, below). However, the trehalose formulations consistently had the highest thermal transitions (Table 6). In addition, the second transition temperature (Tm2) in the histidine formulations was lower than in the citrate and succinate formulations (Table 6).

TABLE 6

DSC Thermal Transition Peaks for Humanized 9E4 as a Function of Buffer and Sugar/Polyol

| Formulation | Tm1 (° C.) | Tm2 (° C.) |
|---|---|---|
| Succinate (pH 6.5) + Sucrose/Mannitol | 72.6 | 83.6 |
| Succinate (pH 6.5) + Sucrose | 72.8 | 83.8 |
| Succinate (pH 6.5) + Trehalose | 72.9 | 83.9 |
| Histidine (pH 6.5) + Sucrose/Mannitol | 72.3 | 82.6 |
| Histidine (pH 6.5) + Sucrose | 72.6 | 82.8 |
| Histidine (pH 6.5) + Trehalose | 72.6 | 83.0 |
| Citrate (pH 6.5) + Sucrose/Mannitol | 71.9 | 83.4 |
| Citrate (pH 6.5) + Sucrose | 72.1 | 83.7 |
| Citrate (pH 6.5) + Trehalose | 72.5 | 83.7 |

RALS measurements were also performed on humanized 9E4 antibodies formulated with the various sugars/polyols in succinate or citrate buffer (pH 6.50. For the succinate buffer, the 240 mM trehalose formulation had the highest transition temperature (77° C.), the 240 mM sucrose formulation had an intermediate transition temperature (76° C.), and the 50 mM sucrose/200 mM mannitol formulation had the lowest transition temperature (75° C.). For the citrate buffer, the 240 mM trehalose formulation and the 50 mM sucrose/200 mM mannitol formulation had the same transition temperature (78° C.), and the 240 mM sucrose formulation had a lower transition temperature (77° C.). The difference of only 1° C. in the thermal transition for the citrate formulations was within the testing variability.

Surfactant.

The effect of polysorbate 20 ("PS20") on thermal stability was tested using DSC and determined to have no impact on the transition temperatures of humanized 9E4 antibody. However, a positive effect of PS20 was observed with respect to shaking stress. Two formulations were tested for their reaction to shaking stress: (A) 20 mM Citrate, pH 6.0, 230 mM trehalose, 0.02% (w/w) PS20; and (B) 25 mM Citrate, pH 6.0, 230 mM trehalose. The formulation with PS20 (Formulation A) provided a lower degree of foam formation and a constant turbidity level even after 24 hours of shaking. Formulation B had a strong foam formation and an increase in turbidity after 3 hours of shaking. Neither formulation led to the generation of visible particles during the shaking study.

Next, the effect of PS20 on formulation turbidity induced by shaking was evaluated. The turbidity of Formulation A did not increase even after 24 hours of shaking. In contrast, the turbidity of Formulation B almost doubled, increasing from 17 FNU (Formazin Nephelometric Units) prior to shaking to 32 FNU after 24 hours of shaking (Table 7).

TABLE 7

Turbidity (FNU) of Humanized 9E4 Antibody
Formulations Prior to and Post Shaking

|  | Initial Value | 3 hrs | 6 hrs | 24 hrs |
|---|---|---|---|---|
| Formulation A | 18 | 18 | 18 | 18 |
| Formulation B | 17 | 20 | 25 | 32 |

Measurements of antibody aggregation prior to and after shaking similarly evidence a stabilizing effect of PS20. The amount of monomeric and aggregated antibody in Formulations A and B was assessed by high performance size exclusion chromatography (HPSEC) prior to shaking and after 3, 6, and 24 hours of shaking. The presence of PS20 in Formulation A correlated with a slight increase (0.2%) in the amount of aggregated antibody (Table 8) and a corresponding decrease (0.2%) in the amount of monomeric antibody (Table 9). In contrast, Formulation B (w/out PS20) exhibited a four-fold higher increase in aggregated antibody (Table 8) and a correspondingly elevated decrease (0.9%) in the amount of monomeric antibody (Table 9).

TABLE 8

Humanized 9E4 Antibody Aggregation
(%) Prior to and Post Shaking

|  | Initial Value | 3 hrs | 6 hrs | 24 hrs |
|---|---|---|---|---|
| Formulation A | 2.6 | 2.6 | 2.6 | 2.8 |
| Formulation B | 2.5 | 2.7 | 3.0 | 3.3 |

TABLE 9

Humanized 9E4 Antibody Monomer Level (%)
Prior to and Post Shaking

|  | Initial Value | 3 hrs | 6 hrs | 24 hrs |
|---|---|---|---|---|
| Formulation A | 97.2 | 97.1 | 97.1 | 97.0 |
| Formulation B | 97.2 | 97.0 | 96.7 | 96.3 |

Thus, the results of the shaking study revealed that PS20 prevents undesirable increases in turbidity and antibody aggregation in humanized 9E4 antibody formulations.

Lyophilization Feasibility Study.

Based on the foregoing analyses, formulations 1-4 (Table 10, below) were selected to evaluate the feasibility of storage of humanized 9E4 antibody in lyophilized form.

TABLE 10

Humanized 9E4 Antibody Test Formulations

| Formulation ID | Formulation Description |
|---|---|
| F1 | 40 mg/ml humanized 9E4 antibody, |
|  | 20 mM succinate, |
|  | 230 mM trehalose, |
|  | 0.02 w % polysorbate 20, |
|  | pH 6.5 |
| F2 | 40 mg/ml humanized 9E4 antibody, |
|  | 20 mM succinate, |
|  | 28 mM sucrose, |
|  | 212 mM mannitol, |
|  | 0.02 w % polysorbate 20, |
|  | pH 6.5 |
| F3 | 40 mg/ml humanized 9E4 antibody, |
|  | 20 mM citrate, |
|  | 230 mM trehalose, |
|  | 0.02 w % polysorbate 20, |
|  | pH 6.0 |
| F4 | 40 mg/ml humanized 9E4 antibody, |
|  | 20 mM citrate, |
|  | 28 mM sucrose, |
|  | 212 mM mannitol, |
|  | 0.02 w % polysorbate 20, |
|  | pH 6.0 |

As an initial step in developing a lyophilization cycle, the thermal properties of the frozen F1-F4 formulations were studied. A Mettler Toledo DSC 821 instrument was used to determine the glass transition (Tg') temperature of each of the formulations. Measurements were made while the following freeze/thaw cycle:

Freezing: 5° C. to 70° C. at 5K/min.

Hold: 3 minutes at −70° C.

Heating: −70° to 25° C. at 5K/min.

Table 11 lists the glass transition temperatures identified in this manner. Formulations 2 and 4 (which include sucrose and mannitol) exhibit a lower Tg' as compared to the trehalose formulations, while the use of different buffers did not significantly impact Tg'. Because of their higher Tg', the trehalose formulations (Formulations 1 and 3) can withstand a higher product temperature during primary drying, which is favorable for the freeze drying process.

TABLE 11

Glass TransitionTemperatures for Formulations
F1 through F4

| Formulation | Tg' (onset) | Tg' (mid point) |
|---|---|---|
| F1 | −27° C. | −26° C. |
| F2 | −35° C. | −34° C. |
| F3 | −36° C. | −25° C. |
| F4 | −34° C. | −33° C. |

Based on the determined glass transition temperatures, two different lyophilization cycles were developed and tested. The first cycle includes a primary drying step that is performed at −10° C. (shelf temperature) (Table 12). The primary drying step in the second cycle is performed at −20° C. (shelf temperature) (Table 13).

TABLE 12

Lyophilization Cycle 1 for Lyophilization Feasibility Study

| | Step No. | Time (hh:mm) | Temp (° C.) | Vacuum MKS (mbar) |
|---|---|---|---|---|
| Loading | 01 | — | 5 | Off |
| Freezing | 02 | 01:30 | 5 | Off |
| | 05 | 02:00 | −50 | Off |
| | 06 | 01:00 | −50 | Off |
| | 07 | 00:30 | −50 | Off |
| Primary Drying | 08 | 00:01 | −50 | 0.10 |
| | 09 | 01:30 | −10 | 0.10 |
| | 10 | 60:00 | −10 | 0.10 |
| Secondary Drying | 11 | 02:00 | 30 | 0.10 |
| | 12 | 08:00 | 30 | 0.10 |
| Total Time | | 76:31 | | |

TABLE 13

Lyophilization Cycle 2 for Lyophilization Feasibility Study

| | Step No. | Time (hh:mm) | Temp (° C.) | Vacuum MKS (mbar) |
|---|---|---|---|---|
| Loading | 01 | — | 5 | Off |
| Freezing | 02 | 01:30 | 5 | Off |
| | 05 | 02:00 | −50 | Off |
| | 06 | 01:00 | −50 | Off |
| | 07 | 00:30 | −50 | Off |
| Primary Drying | 08 | 00:01 | −50 | 0.10 |
| | 09 | 01:30 | −20 | 0.10 |
| | 10 | 45:00 | −20 | 0.10 |
| Secondary Drying | 11 | 04:00 | 30 | 0.10 |
| | 12 | 08:00 | 30 | 0.10 |
| Total Time | | 63:31 | | |

The lyophilization feasibility study was carried out in small scale using an Epsilon 2-12D, GT-12-B Lyophilizer (Christ). Following 0.2 μm filtration, 5.4 ml±0.2 ml aliquots of formulated antibody were added to 20 ml vials (Type I clear glass vials, 20/25 mL, Blow Back, from Schott). The resulting vials had a nominal fill volume of 5.0 ml and a nominal dosage of 200 mg/vial. The intended reconstitution volume following lyophilization was 5.0 ml water. The vials were manually loaded into the lyophilizer and lyophilized according to cycle 1 or cycle 2. Product temperature was monitored using PT100 sensors placed in vials. The cycles were carried out without any deviations. The formulations supercooled to a minimum temperature of −6.5° C. prior to the crystallization of water, after which the formulations were frozen to −50° C. For the primary drying phase, a vacuum of 0.10 mbar (capacitance manometer) was applied, at a shelf temperature of −10° C. (cycle 1) or −20° C. (cycle 2). For cycle 1, these parameters led to a mean product temperature of −28° C. to −25° C. during sublimation. For cycle 2, these parameters led to a mean product temperature below −30° C. during sublimation. The actual duration of primary drying was about 40 hours for both cycles. After primary drying, the shelf temperature was increased to 30 C (secondary drying) to allow for desorption of the unfrozen water. The secondary drying phase was set for a period of 8 hours, with the goal that the lyophilized formulations would have a final moisture level of about 1%. Following lyophilization, the vials were stoppered (Stelmi C1404 6720GC 6 TP3, 20 mm) and sealed (Aluminum flip-off seal, 20 mm).

The trehalose containing formulations were completely amorphous after lyophilization and exhibited some shrinkage. In contrast, the mannitol containing formulations were partially crystalline and exhibited no shrinkage. Cake height for all of the formulations was about 11 mm. Cake mass was about 685 mg (F1), 516 mg (F2), 700 mg (F3), and 520 mg (F4). For all formulations, the cake had a slightly yellow color.

The characteristics of lyophilized formulations produced by cycle 1 and cycle 2 were analyzed and compared, including moisture levels, reconstitution time, number of subvisible particles. See Table 14 (below). In addition, the quality of the lyophilized formulations was compared to the product quality prior to lyophilization. The additional characteristics tested included clarity, pH, osmolarity, amount of monomer vs. aggregate, density, HIC pattern, and activity (data not shown). Overall, no negative impact on product quality was observed following lyophilization and reconstitution: product appearance, color, visible particle level, clarity, pH, osmolarity, protein content, monomer content, HIC pattern, and activity were not significantly altered by the lyophilization process. Furthermore, reconstitution times for formulations lyophilized by both cycle 1 (100-140 seconds) and cycle 2 (100-170 seconds) were acceptable, and measured subvisible particle levels were below the pharmacopeia specifications.

TABLE 14

Results of Lyophilization Feasibility Study, Product Testing Post-Lyophilization

| | Formulation | Cake Appearance | Moisture (%) | Subvisible Particles (per 1 ml) | Reconstitution Time (seconds) |
|---|---|---|---|---|---|
| Cycle 1 | F1 | yellow/brown low shrinkage | 1.09 | 43 (≥10 μm) 1 (≥25 μm) | 123 |
| | F2 | yellow/brown no shrinkage | 1.77 | 83 (≥10 μm) 4 (≥25 μm) | 97 |
| | F3 | yellow/brown low shrinkage | 1.48 | 21 (≥10 μm) 1 (≥25 μm) | 139 |
| | F4 | yellow/brown no shrinkage | 1.94 | 59 (≥10 μm) 1 (≥25 μm) | 104 |

TABLE 14-continued

Results of Lyophilization Feasibility Study, Product Testing Post-Lyophilization

| | Formulation | Cake Appearance | Moisture (%) | Subvisible Particles (per 1 ml) | Reconstitution Time (seconds) |
|---|---|---|---|---|---|
| Cycle 2 | F1 | yellow/brown low shrinkage | 1.07 | 236 (≥10 μm) 4 (≥25 μm) | 104 |
| | F2 | yellow/brown no shrinkage | 1.68 | 276 (≥10 μm) 8 (≥25 μm) | 104 |
| | F3 | yellow/brown low shrinkage | 1.32 | 262 (≥10 μm) 3 (≥25 μm) | 166 |
| | F4 | yellow/brown no shrinkage best appearance | 1.62 | 190 (≥10 μm) 5 (≥25 μm) | 173 |

Because of a tendency for lyophilization cycle 2 to result in longer reconstitution times and slightly higher subvisible particle levels (2-10 μm) for formulations containing mannitol and sucrose, a lyophilization cycle based on a revision of cycle 1 was selected for use in an accelerated stability study. The revised lyophilization cycle included a shorter primary drying phase (step 8) of 40 hours rather than 60 hours, and an extended secondary drying phase (step 10) of 12 hours rather than 8 hours. The longer secondary drying phase was included to further reduce moisture levels in the lyophilized formulations.

Accelerated Stability Study of Lyophilized Formulations.

Formulations F1-F4 (as described in Table 10, above) were lyophilized as described above, except that the lyophilization cycle shown in Table 15 (below) was used. For the accelerated stability study, the lyophilized formulations were stored at 40° C., 75% relative humidity (RH), for a period of one, two, or three months. Following storage, the formulations were reconstituted with water (5.0 ml) and the characteristics of the reconstituted formulations were examined and compared to the characteristics of formulations reconstitute immediately after lyophilization (the "initial values").

TABLE 15

Lyophilization Cycle for Accelerated Stability Study

| | Step No. | Time (hh:mm) | Temp (° C.) | Vacuum MKS (mbar) |
|---|---|---|---|---|
| Loading | 01 | — | 5 | Off |
| Freezing | 02 | 01:30 | 5 | Off |
| | 05 | 02:00 | −50 | Off |
| | 06 | 01:00 | −50 | Off |
| | 07 | 00:30 | −50 | Off |
| Primary Drying | 08 | 00:05 | −50 | 0.10 |
| | 09 | 01:30 | −10 | 0.10 |
| | 10 | 40:00 | −10 | 0.10 |
| Secondary Drying | 11 | 04:00 | 30 | 0.10 |
| | 12 | 12:00 | 30 | 0.10 |
| Total Time | | 62:35 | | |

The cake color of the lyophilized formulations was slightly yellow, consistent with the observations in the lyophilization feasibility study. The cake appearance in all cases was acceptable, with the trehalose formulations (F1 & F3) tending to shrink due to the amorphous character of the lyophilized product (confirmed by X-ray powder diffraction). The monnitol-containing lyophilized formulations (F2 & F4) were partially crystalline and showed essentially no shrinkage. The cake appearance and color of the formulations did not change over the course of storage for three months at 40° C.

The moisture level of the lyophilized formulations prior to reconstitution did not change significantly after three months at 40° C. Moisture levels for the formulations immediately after lyophilization ranged from 0.90% to 1.36%; after three months, they ranged from 0.84% to 1.47%. See Table 16 (below). Differences in the moisture levels observed in different samples of the same formulation are attributed to variance in the testing method. However, formulations containing sucrose and mannitol consistently contained higher levels of moisture than the formulations containing trehalose.

TABLE 16

Moisture Levels of Lyophilized Formulations Following Storage at 40° C.

| | Formulation | | | |
|---|---|---|---|---|
| | F1 20 mM Succinate 230 mM Trehalose 0.02 w % PS20 pH 6.5 | F2 20 mM Succinate 28 mM Sucrose 212 mM Mannitol 0.02 w % PS20 pH 6.5 | F3 20 mM Citrate 230 mM Trehalose 0.02 w % PS20 pH 6.0 | F4 20 mM Citrate 28 mM Sucrose 212 mM Mannitol 0.02 w % PS20 pH 6.0 |
| Initial Value | 0.90 | 1.13 | 1.11 | 1.36 |
| 1 month | 0.85 | 1.18 | 0.94 | 1.48 |
| 2 months | 0.85 | 1.12 | 0.68 | 1.24 |
| 3 months | 0.84 | 1.22 | 0.90 | 1.47 |

Reconstitution times for all of the lyophilized formulations were acceptable, varying between 49 and 97 seconds. The appearance of all of the reconstitute formulations was comparable, with no visible particles observed even after three months at 40° C. In addition, the color of the formulations remained unchanged (<BY5) over the same period of time, as compared to the pre-lyophilized formulations.

No relevant changes in protein concentration, osmolarity and pH were observed for any of the formulations after three months at 40° C. (data not shown). However, differential increases in turbidity were observed. As shown in Table 17 (below), the mannitol-containing formulations (F2 & F4) exhibited larger increases in turbidity (6-7 FNU over three months), while the trehalose-containing formulations (F1 & F3) exhibited smaller increases (only 2 FNU).

TABLE 17

Turbidity of Post-Lyophilized Formulations Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 14 | 16 | 15 | 16 |
| 1 month | 14 | 17 | 15 | 16 |
| 2 months | 14 | 18 | 15 | 18 |
| 3 months | 16 | 23 | 17 | 22 |

Figure 3:
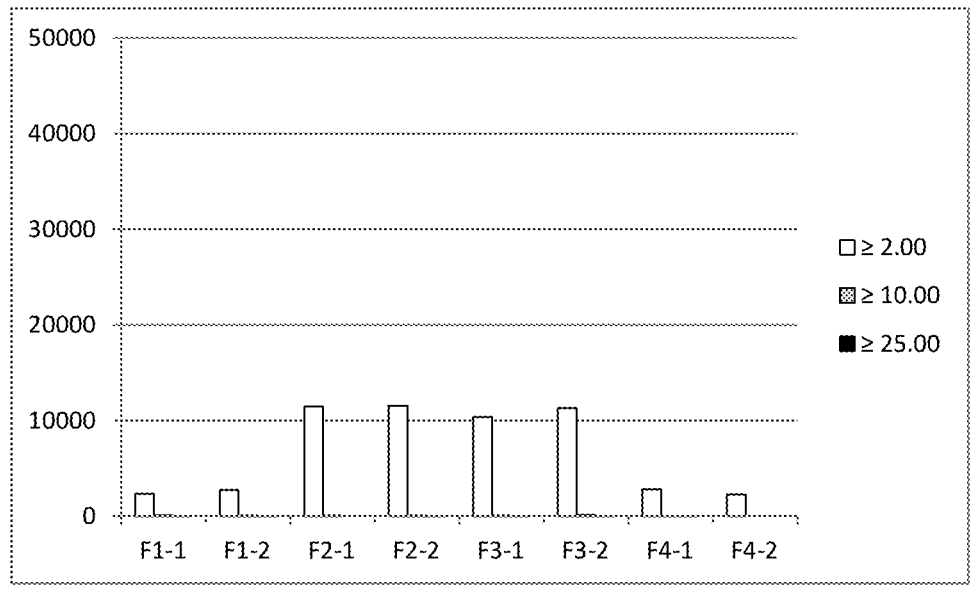
FIG. 3 is a bar graph depicting subvisible particle counts (≥2.0 mm, ≥10.0 mm, and ≥25.0 mm) for formulations F1-F4 (as described in Table 10) following lyophilization and reconstitution, with no storage period.
Figure 4:
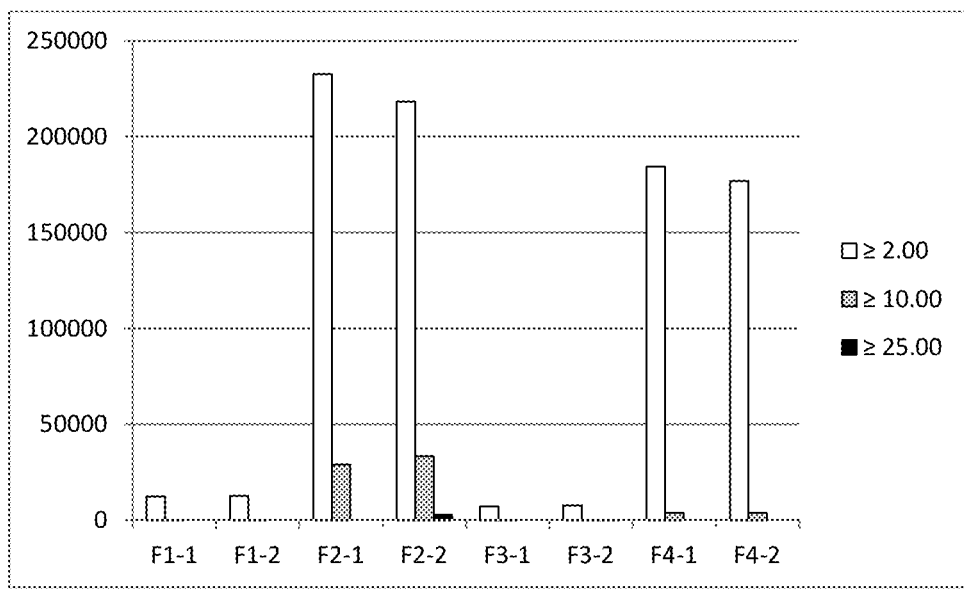
FIG. 4 is a bar graph depicting subvisible particle counts (≥2.0 mm, ≥10.0 mm, and ≥25.0 mm) for formulations F1-F4 (as described in Table 10) following lyophilization, storage at 40° C. for one month, and reconstitution.
Figure 5:
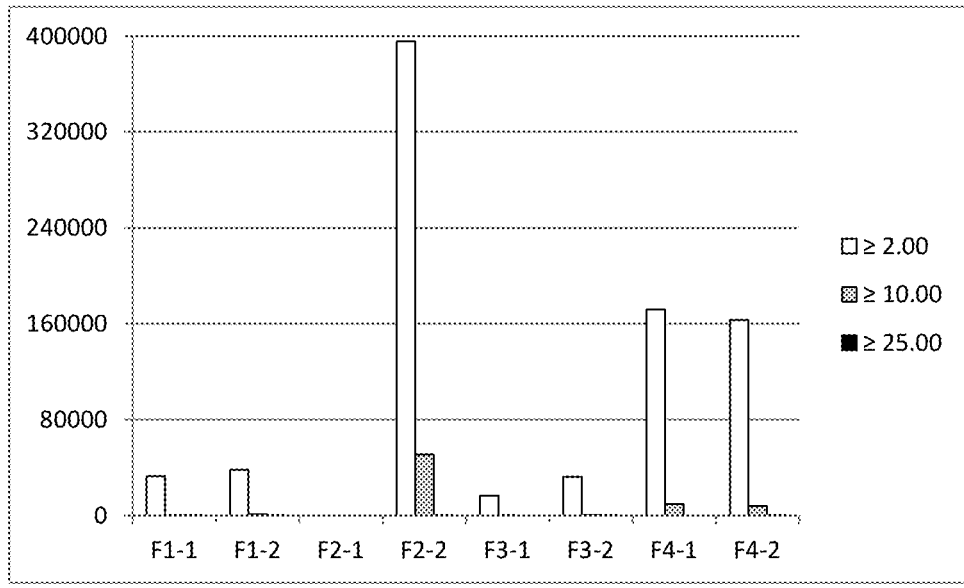
FIG. 5 is a bar graph depicting subvisible particle counts (≥2.0 mm, ≥10.0 mm, and ≥25.0 mm) for formulations F1-F4 (as described in Table 10) following lyophilization, storage at 40° C. for two months, and reconstitution.
Figure 6:
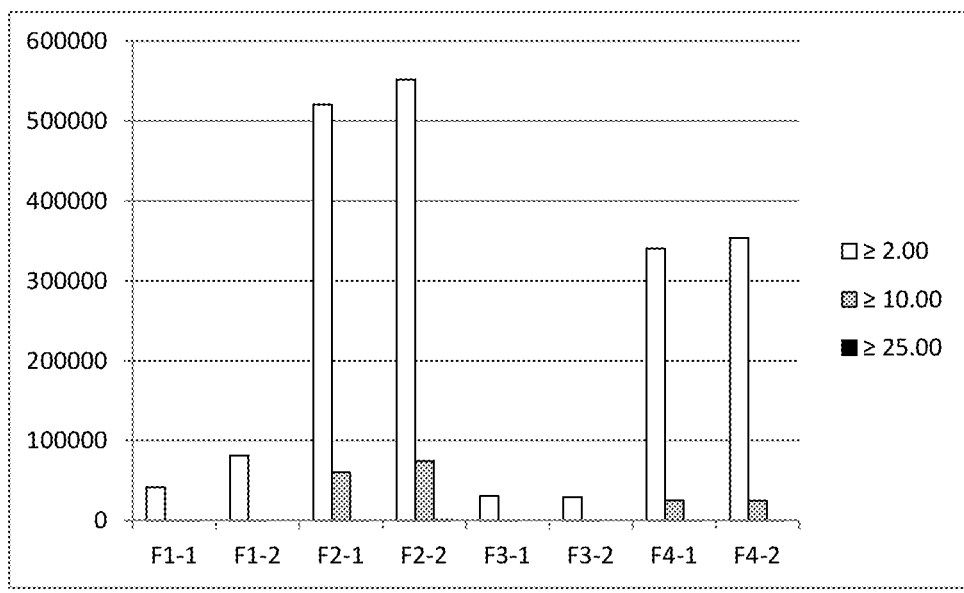
FIG. 6 is a bar graph depicting subvisible particle counts (≥2.0 mm, ≥10.0 mm, and ≥25.0 mm) for formulations F1-F4 (as described in Table 10) following lyophilization, storage at 40° C. for three months, and reconstitution.

Subvisible particles in the reconstituted formulations were measured by the micro-flow imaging (MFI) method. Two individual samples were measured per formulation and time point. For formulations reconstitute right after lyophilization (i.e., without storage at 40° C.), the levels of sub-visible particles are shown in Table 18 (below), with a corresponding bar graph shown in FIG. 3. The levels of sub-visible particles detected in formulations stored for one month, two months, and three months at 40° C. are shown in Tables 19-21, respectively (see below), with the corresponding bar graphs shown in FIGS. 4-6, respectively.

TABLE 18

MFI Data, Initial Values Following Lyophilization

| Particle Size (μm) | F1-1 | F1-2 | F2-1 | F2-2 | F3-1 | F3-2 | F4-1 | F4-2 |
|---|---|---|---|---|---|---|---|---|
| ≥2.00 | 2340 | 2730 | 11470 | 11545 | 10375 | 11285 | 2820 | 2280 |
| ≥10.00 | 110 | 70 | 55 | 50 | 70 | 135 | 25 | 0 |
| ≥25.00 | 10 | 30 | 0 | 10 | 10 | 20 | 10 | 0 |

TABLE 19

MFI Data, Values Following 1 Month of Storage at 40° C.

| Particle Size (μm) | F1-1 | F1-2 | F2-1 | F2-2 | F3-1 | F3-2 | F4-1 | F4-2 |
|---|---|---|---|---|---|---|---|---|
| ≥2.00 | 12370 | 12680 | 232490 | 218280 | 7245 | 7715 | 184365 | 176815 |
| ≥10.00 | 50 | 10 | 28990 | 33455 | 130 | 105 | 3885 | 3925 |
| ≥25.00 | 0 | 0 | 0 | 2955 | 0 | 20 | 65 | 0 |

TABLE 20

MFI Data, Values Following 2 Months of Storage at 40° C.

| Particle Size (μm) | F1-1 | F1-2 | F2-1 | F2-2 | F3-1 | F3-2 | F4-1 | F4-2 |
|---|---|---|---|---|---|---|---|---|
| ≥2.00 | 32995 | 38225 | 0 | 395570 | 16615 | 32445 | 172010 | 163020 |
| ≥10.00 | 410 | 1050 | 0 | 51030 | 45 | 525 | 9775 | 8160 |
| ≥25.00 | 35 | 115 | 0 | 125 | 0 | 75 | 0 | 75 |

TABLE 21

MFI Data, Values Following 3 Months of Storage at 40° C.

| Particle Size (μm) | F1-1 | F1-2 | F2-1 | F2-2 | F3-1 | F3-2 | F4-1 | F4-2 |
|---|---|---|---|---|---|---|---|---|
| ≥2.00 | 41895 | 81355 | 520555 | 551750 | 30740 | 29275 | 340450 | 353695 |
| ≥10.00 | 285 | 330 | 60565 | 74430 | 65 | 55 | 25150 | 24760 |
| ≥25.00 | 10 | 0 | 645 | 820 | 0 | 0 | 35 | 55 |

The MFI analysis revealed that the subvisible particle levels in the tested formulations were comparable right after lyophilization, but that the levels in the mannitol- and sucrose-containing formulations (F2 and F4) increased dramatically after one month, and continued increasing thereafter. As a result, formulation 2 exceeded the Pharmacopeia limits for subvisible particles greater than or equal to 10 microns (≥10.00 μm) and subvisible particles greater than or equal to 25 microns (≥25.00 μm) after just one month, formulation 4 exceeded the Pharmacopeia limits for subvisible particles after two months of storage at 40° C. In contrast, the trehalose-containing formulations (F1 and F3) did not show a significant increase in particle formation and remained below Pharmacopeia limits for subvisible particles for at least three months at 40° C.

Subvisible particles in the four formulations were also measured by light obscuration after two months of storage at 40° C. Light obscuration is a technique known to give differing results than MFI measurements, typically tending to be lower. As shown in Table 22 (below), formulation 2 has the highest levels of subvisible particles detected by light obscuration, while the other formulations has lower, more comparable levels of subvisible particles.

TABLE 22

Light Obscuration Data, Values Following 2 Months of Storage at 40° C.

| | F1<br>20 mM Succinate<br>230 mM Trehalose<br>0.02 w % PS20<br>pH 6.5 | | F2<br>20 mM Succinate<br>28 mM Sucrose<br>212 mM Mannitol<br>0.02 w % PS20<br>pH 6.5 | | F3<br>20 mM Citrate<br>230 mM Trehalose<br>0.02 w % PS20<br>pH 6.0 | | F4<br>20 mM Citrate<br>28 mM Sucrose<br>212 mM Mannitol<br>0.02 w % PS20<br>pH 6.0 | |
|---|---|---|---|---|---|---|---|---|
| Particle Size (μm) | ≥10.00 | ≥25.00 | ≥10.00 | ≥25.00 | ≥10.00 | ≥25.00 | ≥10.00 | ≥25.00 |
| Initial Value | 85 | 5 | 55 | 5 | 275 | 5 | 60 | 0 |
| 2 months | 115 | 5 | 600 | 5 | 280 | 15 | 100 | 0 |

Figure 7:
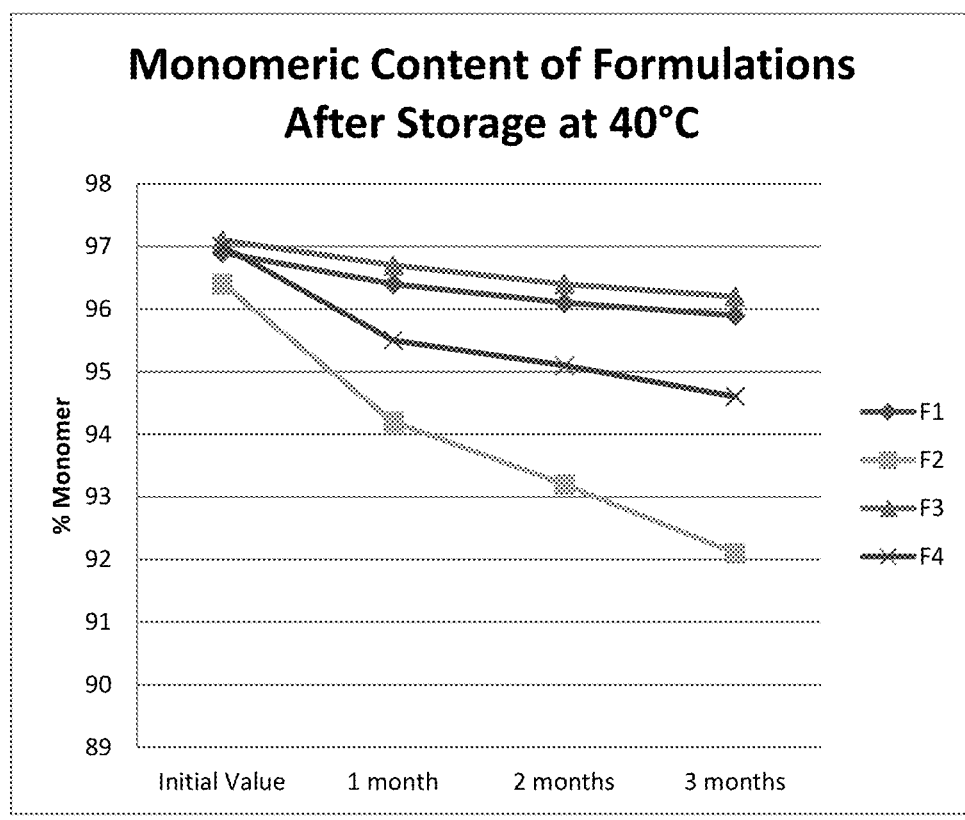
FIG. 7 is a graph depicting the loss of monomeric humanized 9E4 antibody (version H3L3) as a function of formulation (F1-F4, as described in Table 10) and time stored in lyophilized form at 40° C.

The formulations were also analyzed by high performance size exclusion chromatography (HP-SEC) to determine the percentage of antibody in aggregated and monomeric form following storage at 40° C. in the lyophilized state. As shown in Table 23 (below), the percentage of aggregated antibody increased by 2.5% to 4.4% in the mannitol- and sucrose-containing formulations, while increasing by only 1.0% to 1.1% in the trehalose-containing formulations. As the levels of aggregated antibody increased in the formulations, the percentage of monomeric antibody correspondingly decreased. See Table 24. A graphical representation of the amount of monomeric antibody as a function of formulation and time of storage at 40° C. is shown in FIG. 7.

TABLE 23

Antibody Aggregation (Percentage) Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 2.4 | 2.8 | 2.0 | 2.2 |
| 1 month | 2.9 | 5.0 | 2.5 | 3.6 |
| 2 months | 3.1 | 6.0 | 2.8 | 4.1 |
| 3 months | 3.4 | 7.2 | 3.1 | 4.7 |

TABLE 24

Monomeric Antibody (Percentage) Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 96.9 | 96.4 | 97.1 | 97.0 |
| 1 month | 96.4 | 94.2 | 96.7 | 95.5 |
| 2 months | 96.1 | 93.2 | 96.4 | 95.1 |
| 3 months | 95.9 | 92.1 | 96.2 | 94.6 |

The formulations were also characterized by hydrophobicity interaction chromatography (HIC) over the course of their storage at 40° C. For each formulation, a pre-peak (relatively hydrophilic), a main peak, and a post-peak (relatively hydrophobic) can be detected by HIC. Changes in protein structure over time can be monitored through the changes in the area of each of the peaks that occurs. The results of the HIC analysis are shown in Tables 25-27 (below). The change in the area of the pre-peak was comparable for each of the formulations. The changes in the main peak and the post-peak areas were more significant, differing between the trehalose-containing and mannitol/sucrose-containing formulations. In particular, the mannitol/sucrose-containing formulations (F2 and F4) exhibited 8.4% and 5.4% decreases in main peak area, respectively, over the three month storage period. In contrast, the trehalose-containing formulations (F1 and F3) exhibited 4.7% and 4.5% decreases in main peak area, respectively, over the same period of time. Most of the protein previously in the main peak of the mannitol/sucrose-containing formulations shifted to the hydrophobic post-peak, with the post-peak areas of formulations F2 and F4 increasing by 6.4% and 4.6%, respectively.

TABLE 25

HIC Data, Pre-Peak Area (Percentage) Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 7.4 | 7.3 | 8.3 | 8.4 |
| 1 month | 7.6 | 7.8 | 9.2 | 9.5 |
| 2 months | 7.4 | 8.1 | 8.3 | 8.8 |
| 3 months | 9.8 | 9.3 | 9.9 | 9.3 |

TABLE 26

HIC Data, Main Peak Area (Percentage) Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 87.8 | 87.7 | 87.5 | 87.3 |
| 1 month | 87.1 | 85.3 | 86.0 | 84.9 |
| 2 months | 87.1 | 84.1 | 86.6 | 85.3 |
| 3 months | 83.1 | 79.3 | 83.0 | 81.8 |

TABLE 27

HIC Data, Post-Peak Area (Percentage) Following Storage at 40° C.

| | Formulation | | | |
|---|---|---|---|---|
| | F1<br>20 mM Succinate<br>230 mM Trehalose<br>0.02 w % PS20<br>pH 6.5 | F2<br>20 mM Succinate<br>28 mM Sucrose<br>212 mM Mannitol<br>0.02 w % PS20<br>pH 6.5 | F3<br>20 mM Citrate<br>230 mM Trehalose<br>0.02 w % PS20<br>pH 6.0 | F4<br>20 mM Citrate<br>28 mM Sucrose<br>212 mM Mannitol<br>0.02 w % PS20<br>pH 6.0 |
| Initial Value | 4.7 | 5.0 | 4.2 | 4.3 |
| 1 month | 5.3 | 6.9 | 4.8 | 5.7 |
| 2 months | 5.5 | 7.8 | 5.0 | 6.0 |
| 3 months | 7.1 | 11.4 | 7.1 | 8.9 |

The formulations were also characterized by isoelectric focusing and capillary imaging (iCE). Each of the formulations displayed three-peak pattern, including an acidic peak, a main peak, and a basic peak. As shown in Table 28, Formulation 1 displayed the least change in peak pattern during three months of storage at 40° C., while Formulations 2-4 displayed large increases in the basic peak area over time.

TABLE 28 iCE Data Following Storage at 40° C.

| Formulation | Sample | Acidic Peak Area | Main Peak Area | Basic Peak Area |
|---|---|---|---|---|
| F1 | Initial Value | 41.8 | 53.0 | 5.2 |
| 20 mM Succinate | 1 month | 41.4 | 51.5 | 7.1 |
| 230 mM Trehalose | 2 months | 39.9 | 52.5 | 7.6 |
| 0.02 w % PS20 | 3 months | 37.0 | 57.1 | 5.9 |
| pH 6.5 | | | | |
| F2 | Initial Value | 40.2 | 55.3 | 4.5 |
| 20 mM Succinate | 1 month | 44.9 | 48.2 | 6.9 |
| 28 mM Sucrose | 2 months | 48.1 | 44.9 | 7.1 |
| 212 mM Mannitol | 3 months | 40.3 | 50.3 | 9.4 |
| 0.02 w % PS20 | | | | |
| pH 6.5 | | | | |
| F3 | Initial Value | 39.8 | 56.4 | 3.8 |
| 20 mM Citrate | 1 month | 36.4 | 56.3 | 7.3 |
| 230 mM Trehalose | 2 months | 37.5 | 53.5 | 9.0 |
| 0.02 w % PS20 | 3 months | 35.7 | 55.4 | 9.0 |
| pH 6.0 | | | | |
| F4 | Initial Value | 43.0 | 52.5 | 4.5 |
| 20 mM Citrate | 1 month | 42.1 | 49.0 | 8.9 |
| 28 mM Sucrose | 2 months | 45.3 | 44.9 | 9.8 |
| 212 mM Mannitol | 3 months | 34.5 | 54.7 | 11.9 |
| 0.02 w % PS20 | | | | |
| pH 6.0 | | | | |

The antigen-binding activity of the antibody in each of the formulations was also examined. The antibody retained high antigen-binding activity throughout the three months of storage at 40° C., regardless of the formulation.

The formulations were also tested for aggregate formation during ultrafiltration/diafiltration (UF/DF processing). Formulation 3 exhibited the least amount of aggregate formation, while formulation 2 exhibited the most; formulations 1 and 4 exhibited intermediate amounts of aggregation (data not shown).

Considering all of the accelerated stability data, formulations F1 and F3 display a superior stability after 3 months of storage, as compared to formulations F2 and F4. This is a reflection of the fact that formulations F2 and F4 (the mannitol/sucrose-containing formulations) display relatively poor stability as detected by turbidity, HP-SEC, subvisible particles, HIC, and iCE. Comparing formulations F1 and F3, one significant difference is that F1 tends to generate slightly more aggregates than F3 during ultrafiltration/diafiltration processing. Therefore, F3 was selected as a preferred formulation.

Formulation Stability With Respect to Freezing and Thawing.

Formulation F3 was next tested for its ability to stabilize humanized 9E4 antibody with respect to freezing and thawing. To this end, humanized 9E4 antibody was purified and resuspended in formulation F3. 20 ml of F3 containing humanized 9E4 at 40 mg/ml was then filled into Sartorius Stedim Flexboy 30 ml bags, and the bags were frozen at −40° C. Up to five freeze/thaw cycles were performed per bag. Analytical testing of the humanized 9E4 antibody in formulation F3 was performed prior to freezing and after 1, 3 and 5 freeze/thaw cycles. No significant changes were detected after up to three freeze-thaw cycles. After five freeze/thaw cycles, a slight increase in the level of aggregated antibody (0.2%) was detected and minor changes in the HIC and iCE patters were observed. All other assay results, including visual inspection for color and visible particles, clarity, UV scan, HP-SEC, osmolality, pH, sub-visible particle counts, and antibody activity, did not change after five freeze-thaw cycles.

Various changes in form and details can be made therein without departing from the spirit and scope of the invention. Unless otherwise apparent from the context, any embodiment, aspect, element, feature, step or the like can be used in combination with any other. Insofar as information associated with a citation may change with time, the information associated with the citation at the earliest effective filing date is meant, the earliest effective filing date for a citation meaning the filing date of the present application or earlier priority application disclosing the citation. All references, issued patents and patent applications cited within the body of the instant specification are hereby incorporated by reference in their entirety, for all purposes. Any embodiment, aspect, feature, element, step or the like can be combined with any other unless the context indicates otherwise. When a composition is said to comprise certain specified components, the application should be read unless the context requires otherwise as disclosing that in the alternative, the composition may consist of or consist essentially of the specified components. For example, when an antibody chain is said to have an amino acid sequence comprising a specified SEQ ID NO., it should be understood unless the context requires otherwise that alternatively the antibody chain can consist of or consist essentially of the SEQ ID NO.

What is claimed is:

1. A pharmaceutical formulation comprising:
   (a) an antibody comprising a light chain having the amino acid sequence comprising the sequence of SEQ ID NO: 5 and a heavy chain having the amino acid sequence comprising the sequence of SEQ ID NO: 10, wherein the antibody is present at a concentration of about 40 mg/ml and the antibody is in the form of a tetramer comprising two copies of the heavy chain and two copies of the light chain;
   (b) citrate buffer present at a concentration of about 20 mM;
   (c) trehalose present at a concentration of about 230 mM; and
   (d) polysorbate 20 present at a concentration of about 0.02% by weight;
   wherein the formulation is characterized by a pH of about 6.0;
   wherein about indicates variation of ±5%; and
   wherein at least 95% of protein appears as a single peak on high performance size exclusion chromatography after storage for at least 30 days at 38-42° C., storage for at least a year at 20-24° C., and/or storage for at least three years at 2-4° C.

2. The formulation of claim 1, wherein the citrate buffer comprises sodium citrate dihydrate and citric acid monohydrate.

3. The formulation of claim 2, wherein the sodium citrate dihydrate is present at a concentration within the range from about 15 mM to about 20 mM and the citric acid monohydrate is present at a concentration within the range from about 2 mM to about 6 mM.

4. The formulation of claim 1, which is characterized by an osmolality of about 335 mOsm/kg.

5. The formulation of claim 1, which further comprises a bulking agent.

6. The formulation of claim 1, which is sterile.

7. The formulation of claim 1, wherein:
   (a) the antibody comprises a light chain having the amino acid sequence comprising SEQ ID NO: 29 and a heavy chain having the amino acid sequence comprising SEQ ID NO: 32 with or without the C-terminal lysine, and which is present at a concentration of about 40 mg/mL;
   (b) a citrate buffer present at a concentration of 20 mM;
   (c) trehalose present at a concentration of 230 mM;
   (d) polysorbate 20 present at a concentration of 0.02%; and
   (e) a pH of 6.0.

8. A lyophilized formulation of an antibody, comprising:
   (a) an antibody comprising a light chain having the amino acid sequence comprising SEQ ID NO: 5 and a heavy chain having the amino acid sequence comprising SEQ ID NO: 10 and the antibody is in the form of a tetramer comprising two copies of the heavy chain and two copies of the light chain;
   (b) citrate;
   (c) trehalose; and
   (d) polysorbate 20.

9. The lyophilized formulation of claim 8, which, on adding water, reconstitutes to a formulation having a pH of between about 5.5 to about 6.5.

10. The lyophilized formulation of claim 9, wherein the formulation has a pH of about 6.0 when reconstituted.

11. The lyophilized formulation of claim 8, comprising about 10 mg to about 40 mg of the antibody.

12. The lyophilized formulation of claim 8, wherein the polysorbate 20 is present in an amount within the range from about 0.01% to about 0.05% by weight.

13. The lyophilized formulation of claim 8 which is reconstitutable by adding water to an aqueous solution comprising:
(a) an antibody comprising a light chain having the amino acid sequence comprising SEQ ID NO: 29 and a heavy chain having the amino acid sequence comprising SEQ ID NO: 32, with or without the C-terminal lysine, and which is present at a concentration of about 40 mg/mL;
(b) a citrate buffer present at a concentration of about 20 mM;
(c) trehalose present at a concentration of about 230 mM;
(d) polysorbate 20 present at a concentration of about 0.02%; and
(e) a pH of about 6.0.

14. The lyophilized formulation of claim 13, wherein the lyophilized formulation comprises about 200 mg of the antibody and enables reconstitution with sterile water.

15. The lyophilized formulation of claim 8, comprising:
(a) 200 mg of the antibody;
(b) 25 mg of sodium citrate dihydrate;
(c) 2.15 mg citric acid monohydrate;
(d) 435 mg trehalose dihydrate; and
(e) 1 mg polysorbate 20.

16. A pharmaceutical product, comprising:
(a) a vial comprising in powder form:
(i) about 200 mg antibody;
(ii) about 25 mg sodium citrate dehydrate;
(iii) about 2.15 mg citric acid monohydrate;
(iv) about 435 mg trehalose dehydrate; and
(v) about 1 mg polysorbate 20;
(b) instructions for reconstitution of the antibody; and
(c) instructions for preparing the reconstituted antibody for infusion,
wherein:
(i) the antibody comprises a light chain having the amino acid sequence comprising SEQ ID NO: 29 and a heavy chain having the amino acid sequence comprising SEQ ID NO: 32, with or without the C-terminal lysine; and
(ii) the reconstitution instructions require initial reconstitution with water to a volume of about 5 mL.

17. The formulation of claim 1, wherein:
(a) the antibody comprises a light chain having the amino acid sequence comprising SEQ ID NO: 29 and a heavy chain having the amino acid sequence comprising SEQ ID NO: 31 with or without the C-terminal lysine, and which is present at a concentration of about 40 mg/mL;
(b) a citrate buffer present at a concentration of about 20 mM;
(c) trehalose present at a concentration of about 230 mM;
(d) polysorbate 20 present at a concentration of about 0.02%; and
(e) a pH of about 6.0.

18. The lyophilized formulation of claim 8 which is reconstitutable by adding water to an aqueous solution comprising:
(a) an antibody comprising a light chain having the amino acid sequence comprising SEQ ID NO: 29 and a heavy chain having the amino acid sequence comprising SEQ ID NO: 31, with or without the C-terminal lysine, and which is present at a concentration of about 40 mg/mL;
(b) a citrate buffer present at a concentration of about 20 mM;
(c) trehalose present at a concentration of about 230 mM;
(d) polysorbate 20 present at a concentration of about 0.02%; and
(e) a pH of about 6.0.

19. The lyophilized formulation of claim 8, comprising about 40 mg to about 1000 mg of the antibody.

20. The lyophilized formulation of claim 8, comprising:
(a) 200 mg of the antibody;
(b) 25 mg of sodium citrate dihydrate;
(c) 3.15 mg citric acid monohydrate;
(d) 435 mg trehalose dihydrate; and
(e) 1 mg polysorbate 20.

21. A pharmaceutical product, comprising:
(a) a vial comprising in powder form:
(i) about 200 mg antibody;
(ii) about 25 mg sodium citrate dehydrate;
(iii) about 3.15 mg citric acid monohydrate;
(iv) about 435 mg trehalose dehydrate; and
(v) about 1 mg polysorbate 20;
(b) instructions for reconstitution of the antibody; and
(c) instructions for preparing the reconstituted antibody for infusion,
wherein:
(i) the antibody comprises a light chain having the amino acid sequence comprising SEQ ID NO: 29 and a heavy chain having the amino acid sequence comprising SEQ ID NO: 32, with or without the C-terminal lysine; and
(ii) the reconstitution instructions require initial reconstitution with water to a volume of about 5 mL.

22. The formulation of claim 1, wherein less than about 5% of the antibody is present as an aggregate in the formulation.

23. The formulation of claim 1 consisting essentially of the antibody, citrate buffer, trehalose and polysorbate.

* * * * *